United States Patent [19]
Furuki et al.

[11] Patent Number: 5,411,709
[45] Date of Patent: May 2, 1995

[54] GAS DETECTOR

[75] Inventors: Makoto Furuki; Lyong S. Pu, both of Kanagawa, Japan

[73] Assignee: Fuji Xerox Co., Ltd., Tokyo, Japan

[21] Appl. No.: 860,754

[22] Filed: Mar. 24, 1992

[30] Foreign Application Priority Data

Mar. 25, 1991 [JP] Japan .................................. 3-084658
Aug. 23, 1991 [JP] Japan .................................. 3-237113
Feb. 4, 1992 [JP] Japan .................................. 4-047634

[51] Int. Cl.$^6$ ........................................... G01N 21/64
[52] U.S. Cl. ....................................... 422/91; 422/83; 422/88; 436/172
[58] Field of Search ............... 422/82.07, 82.08, 82.11, 422/88, 83, 91; 436/172; 250/227.14, 227.21

[56] References Cited

U.S. PATENT DOCUMENTS 4,897,541  1/1990  Phillips ........................... 250/227.21

FOREIGN PATENT DOCUMENTS 2-243944  9/1990  Japan .

OTHER PUBLICATIONS

"Surface Acoustic Wave Sensors Incorporating Langmuir–Blodgett Films", Thin Solid Films, 160 (1988) pp. 445–452.

"Simultaneous Electrical Conductivity and Piezoelectric Mass Measurements on Iodine–Doped Phthalocyanine Langmuir–Blodgett Films", Langmuir, vol. 2, No. 4 (1986) pp. 513–519.

*Primary Examiner*—Jill A. Warden
*Attorney, Agent, or Firm*—Finnegan, Henderson Farabow, Garrett & Dunner

[57] ABSTRACT

A gas detector for simultaneously detecting a kind of gas to be detected and a gas concentration by simultaneously effecting adsorption-measuring type gas detection and optical gas detection. The gas detector comprises a gas detecting element having a gas sensitive thin film disposed on a piezoelectric vibrating element and adapted to generate fluorescence or phosphorescence when irradiated with a light, an oscillating unit for oscillating the piezoelectric vibrating element, a frequency detecting unit for detecting an oscillation frequency of the piezoelectric vibrating element, a light emitting element for irradiating the gas sensitive thin film with light and a light receiving element for receiving the fluorescence or phosphorescence generated from the gas sensitive thin film and adapted to detect the intensity of the fluorescence or phosphorescence. The gas detecting element is disposed in a reaction tank provided with a gas passageway and having a light transmissive window.

6 Claims, 9 Drawing Sheets

GAS DETECTOR

BACKGROUND OF THE INVENTION

The present invention relates to a gas detector capable of simultaneously detecting the kind and concentration of a gas to be detected, by using as a gas sensitive material a thin film containing organic dye molecules.

Among conventional gas detectors, a contact combustion type or a semiconductor type has been a mainstay. In these gas detectors, a gas sensitive material is formed by making use of an inorganic semiconductor, a ceramic, or a precious metal catalyst. Meanwhile, gas detectors using an organic molecule thin film as the gas sensitive material have been proposed in recent years. It is known that certain types of organic dye molecules interact with an oxidizing or reducing gas with a certain degree of selectivity, and their electrical or optical characteristics change. For instance, an application to $NO_x$, $SO_x$ gas detectors has been proposed by making use of the change in electrical characteristics of phthalocyanine. Furthermore, an absorption-measuring type gas detector has also been proposed in which a gas sensitive thin film formed of organic molecules is formed on a piezoelectric vibrating element such as a quartz resonator or a surface acoustic wave device (SAW device), and a gas exhibiting a high adsorptivity with respect to the gas sensitive thin film, such as an oxidizing or reducing gas or organic solvent-based gases of various kinds, is detected as a change in the oscillation frequency of the piezoelectric vibrating element.

For instance, B. Holcroft and G. G. Roberts have confirmed that the oscillation frequency of a SAW device decreases by approx. 1 kHz by accumulating a silicon phthalocyanine LB film on a 98.6 MHz delay-line type SAW device and placing the same in a 100 ppm $NO_2$ gas atmosphere, and that the change in the frequency is proportional to the concentration of the reactive gas. In addition, Moriizumi et al. have made an attempt in which different organic thin films are formed on a quartz resonator, and the pattern of changes in the oscillation frequency obtained from an adsorption-measuring type gas detector when organic gases of various kinds were brought into contact with the organic thin films was learned through a neural network model using back propagation, so as to discriminate the kind of gas. Meanwhile, the present inventors have proposed a novel optical gas detector in Published Unexamined Japanese Patent Application No. 243944/1990. This apparatus makes use of a phenomenon in which when an organic dye thin-film element is irradiated with excitation light, and an $NO_2$ gas is brought into contact with the organic dye thin film, the intensity of fluorescence or phosphorescence emitted from the organic dye thin film changes. According to this apparatus, the fluorescence or phosphorescence emitted from the organic dye thin film changes noticeably owing to a slight electronic interaction between the dye molecules in the thin film and the gas molecules adsorbed on the thin film. Hence, by measuring the change in the fluorescence intensity or phosphorescence intensity, it is possible to detect a gas having a very low concentration. Furthermore, in a case where dye molecules are located adjacent to each other in the organic dye thin film and exist by forming a certain associated condition, its effect is amplified. If use is made of an organic dye thin film which assumes an associated condition formed by a very large number of molecules as in the case of J-aggregate(s), in particular, its amplification factor reaches several tens to hundreds fold.

In accordance with a conventional gas detecting method using a piezoelectric vibrating element, it is possible to ascertain an amount of a subject gas adsorbed on an organic thin film serving as a gas sensitive material. If a target gas is restricted, or the organic thin film on the piezoelectric vibrating element used has a particularly high distribution factor with respect to that gas, it is possible to measure the gas concentration quantitatively to a certain extent. In a case where the kind of gas is not restricted, or a coexisting gas is present, however, only limited information is obtained.

Meanwhile, an attempt has been made in which a plurality of arrangements in which an organic thin film is formed on such a piezoelectric vibrating element are prepared so as to discriminate the kind of gas on the basis of a difference in the amount of adsorption on the respective films. However, to distinguish between the difference of the gas concentration and the kind of gas only from the difference in the amount of adsorption, not only are required a multiplicity of gas detecting elements, but a burden imposed on the learning elements for effecting pattern recognition becomes large since the meaning of the signal patterns is difficult.

Meanwhile, in accordance with an optical gas detecting method making use of a change in fluorescence or phosphorescence, the kind of gas which imparts a change to the fluorescence or phosphorescence of the gas sensitive material can be detected with very high sensitivity. In addition, the difference in the property of the gas can be discriminated in the form of an increase or decrease in fluorescence or phosphorescence, and the gas concentration can be measured quantitatively from a rate of change thereof to a certain extent. With respect to the kind of gas which imparts no change to the optical characteristics, however, no signal is obtained.

SUMMARY OF THE INVENTION

The present invention has been accomplished in view of the above-described drawbacks accompanying the conventional art.

Accordingly, an object of the present invention is to provide a gas detector capable of selecting and detecting a gas which is merely adsorbed and gas molecules involving an electronic interaction with dye molecules, by forming a gas sensitive thin film constituted by organic dye molecules on a piezoelectric vibrating element and by simultaneously measuring a change in optical characteristics in addition to measurement of an amount of adsorption.

Another object of the present invention is to provide a gas detector which accurately effects the discrimination of the type of gas and concentration detection by complicating a gas detecting element, and which effectively operates even in a complicated situation.

Still another object of the present invention is to provide a gas detector which facilitates both fabrication and measurement, has both safety and stability with respect to various conditions, and is difficult to be affected by noise.

The present inventors completed the present invention after discovering that by combining an adsorption-measuring type gas detecting method and an optical gas detecting method for measuring a change in the intensity of fluorescence or phosphorescence, it is possible to compensate for the respective drawbacks, and to accurately detect the property of a gas to be detected and a concentration thereof.

The gas detector in accordance with the present invention comprises: a gas detecting element having a vibrating member and a gas sensitive thin film disposed on the vibrating member and adapted to generate fluorescence or phosphorescence when irradiated with light; vibrating means for vibrating the vibrating member; frequency detecting means for detecting an oscillation frequency of the vibrating member; light applying means for applying light to the gas sensitive thin film; and light detecting means for receiving the fluorescence or phosphorescence generated from the gas sensitive thin film and adapted to detect the intensity of the fluorescence or phosphorescence.

In accordance with the gas detector of the present invention, the relationship between changes in the intensity of fluorescence or phosphorescence and changes in the oscillation frequency is stored in advance, and by making a comparison between the same and a signal produced as a result of contact with a gas to be detected, the discrimination of the kind of gas and concentration measurement can be effected simply. In addition, even with respect to the kind of gas which is not stored in advance, the property of the gas can be determined simply from the direction of a change in the intensity of fluorescence or phosphorescence.

In addition, if a plurality of organic thin films serving as a gas sensitive material are prepared, an output which facilitates an understanding of the significance of a change in the intensity of fluorescence or phosphorescence can be obtained. Hence, by allowing output patterns thereof to be learned, it is possible to cope with a more complicated situation, and the separation of the kind of gas can be improved. Thus, in the processing of signals from such a plurality of kinds of gas detecting elements, a determination can be made deterministically by univocally comparing the respective outputs with the data stored. In addition, if the umber of signals increases, a pattern recognition method using a statistical multi-quantity analysis method becomes effective. Also, if the technique of a neural network model (e.g. back propagation), which has recently come to attract attention, is used, the pattern recognition is possible without devising a complicated algorithm.

Furthermore, if an attempt is made to allow the optical gas detecting method and the adsorption-measuring type gas detecting method to be applied simultaneously with respect to one gas sensitive thin film, it is possible to measure a ratio of respective outputs in a transient manner. Hence, the discrimination and recognition of the kind of gas become more advantageous, and a useful guideline can be obtained in the selection of the gas sensitive thin film. Accordingly, it becomes possible to effectively obtain much information by a combination of gas sensitive thin films of a smaller number of kinds. In addition, it is readily possible to eliminate noise attributable to factors other than the gas in the outputs of a change in the intensity of fluorescence or phosphorescence and a change in the oscillation frequency through simultaneous measurement.

DESCRIPTION OF THE PREFERRED EMBODIMENTS

Figure 1:
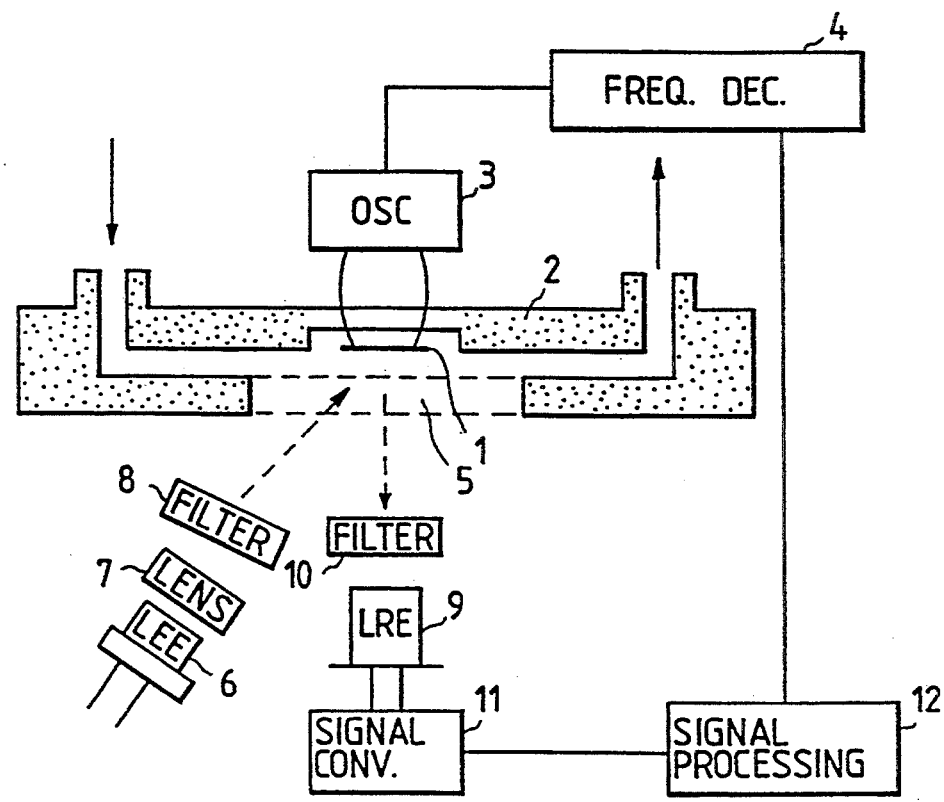
FIG. 1 is a schematic diagram illustrating a basic arrangement of a gas detector in accordance with the present invention.

A detailed description will be given hereafter of the present invention.

In the gas detector in accordance with the present invention, the gas detecting element is arranged such that a gas sensitive thin film for generating fluorescence or phosphorescence when irradiated with light is disposed on a vibrating member serving as a substrate. A thin film containing an organic dye for generating fluorescence or phosphorescence is used as this gas sensitive thin film. In the present invention, this gas sensitive thin film is preferably a monomolecular laminated film of an organic dye. This gas sensitive thin film has a property of adsorbing a gas to be detected, such as oxidizing and reducing gases including $NO_x$, $SO_x$, $C_2$, $O_3$, $O_2$, $CO_2$, CO, an organic acid, $NH_3$, $H_2S$, an organic amine, and the like, organic solvent gases including various alcohols, acetone, chloroform, trichloroethylene, hexane, benzene, toluene, and the like, perfumes of such as esters, anesthetics, and so on. The gas sensitive thin film should be desirably such that the oscillation frequency of the vibrating member changes reversibly with the adsorption of the gas to be detected. Furthermore, the gas sensitive thin film should be desirably such that gas molecules adsorbed cause an electronic interaction with the dye molecules in the thin film, and the intensity of fluorescence or phosphorescence changes reversibly. In this respect, the gas sensitive thin film is preferably as thin as possible so as to enhance the reversibility of the adsorption of the gas molecules. In addition, it is preferred that the dye used for generating fluorescence or phosphorescence adsorb the gas molecules to be detected, and possess high chemical stability.

When an oxidizing or reducing gas is adsorbed on an organic dye, a strong electronic interaction acts between the gas molecules adsorbed and the dye molecules, and a noticeable change in fluorescence or phosphorescence, for instance, is observed. In addition, there are cases where an obverse change in the fluorescence or phosphorescence is observed depending on the difference of the property and kind of the gas adsorbed. Some kinds of dye molecules display a very strong interaction with respect to a particular gas. Accordingly, if the change in the oscillation frequency of the piezoelectric vibrating element is measured, the amount of adsorption of the gas to be detected on the thin film can be detected. If the change in the intensity of fluorescence or phosphorescence generated from the thin film is measured, it is possible to detect the difference in the property and kind of the gas to be detected.

As the dye which is used in the present invention for generating fluorescence or phosphorescence, various known dyes, such as a squaryliumdye, a cyanine dye, a merocyanine dye, a phthalocyanine dye, a porphyrin dye, an azo dye, an acridine dye, a pyrene dye, a perylene dye, an indigo dye, and a stylbene dye, sufficiently meet the aforementioned conditions and may be used advantageously in the gas detector of the present invention. As the conditions, it is essential that the dye is chemically stable, as described above, that it generates sufficiently strong fluorescence or phosphorescence, and that it allows the formation of a thin film.

In the gas detector of the present invention, a quartz resonator and a piezoelectric vibrator such as a delay-line type or reflector type surface acoustic wave device (SAW device) may be used as a vibrating member serving as a substrate on which the above-described gas sensitive thin film is formed.

In addition, an oscillator circuit is used as the vibrating means for vibrating the piezoelectric vibrating element which is the vibrating member, and as the oscillator circuit, it is possible to use a circuit using a TTL or a C-MOS, a transistor circuit, and a circuit jointly using a coil.

It is necessary that an oscillation signal of the piezoelectric vibrating element can be fetched from the oscillator circuit. As for the oscillation signal fetched, the oscillation frequency is detected by the frequency detecting means. That is, with respect to the oscillation signal fetched, the frequency is measured by a circuit or device for counting the frequency, and is converted to a gas concentration by simple signal processing. The stability of the oscillation frequency obtained by a combination of the piezoelectric vibrating element, oscillator circuit, and frequency counter is preferably as high as possible. For instance, in a case where 10 MHz quartz resonator is used, it is desirable that the stability falls within $\pm 0.1$–$1$ Mz or thereabouts.

Furthermore, in order to oscillate a plurality of vibrating members simultaneously, the power supply may be used in common, but it is preferred that oscillator circuits be used independently so that the individual oscillations will not interfere each other. In a case where a SAW device is used as the vibrating member, a plurality of vibrating members may be built on one substrate, and different gas sensitive thin films are formed on the respective vibrating members by way of a space-saving measure. In addition, as the electrode material of the vibrating material, it is preferable to use a metal with high corrosion resistance and low adsorptivity, and to use the quartz of the piezoelectric material which is provided with surface polishing or surface treatment, as necessary, so as to lower adsorptivity.

In addition, in the gas detector of the present invention, a light emitting element is used as the light irradiating means for irradiating the gas sensitive thin film of the gas detecting element with light, and is used as an excitation light source for generating fluorescence or phosphorescence from the gas sensitive thin film, as described above. Specifically, as the light emitting element, it is possible to use a semiconductor laser device, a gas laser, a combination of a semiconductor laser device and an SHG device, an LED, and a device in which light from a white light lamp such as a xenon or halogen lamp is spectrally diffracted, and so on.

The fluorescence or phosphorescence generated as described above is received by the light detecting means. The light detecting means is provided with the light receiving element and, in that case, a filter for separating the fluorescence or phosphorescence and the excitation light is used. This filter is disposed in an optical path between the gas detecting element and the light receiving element. As the filter, it is preferable to use a filter which cuts off the light issuing from the light emitting element, and transmitting fluorescence or phosporescence issuing from the gas detecting element and cutting off the light having a wavelength longer than that of fluorescence or phosphorescence.

In the present invention, in a case where components other than the light having a wavelength necessary for excitation are issued from the light emitting element used, a filter for cutting off the same may be further used. That is, a filter which has the property of allowing mainly the light having a wavelength in the vicinity of a main emission wavelength emitted from the light emitting element to be transmitted therethrough, and of cutting off mainly the light other than the light having a wavelength in the vicinity of the main emission wavelength emitted from the light emitting element may be disposed in the optical path between the light emitting element and the gas detecting element. In that case, it is preferable to dispose of the filter in such a manner that the light incident upon the filter is made incident at an angle perpendicular to the filter surface. By virtue of these optical systems, the intensity of fluorescence or phosphorescence is fetched as an output of the light receiving element at a very low noise level. In addition, in a case where signals from a plurality of gas detectors are fetched simultaneously, light emitting elements and light receiving elements may be prepared separately, or if their optical wavelengths are common, in the case of the light emitting element, the element may be shared by being divided by a half mirror or the like. In the case of the light receiving element, the element may be shared through time sharing. In addition, an arrangement may be alternatively provided such that gas detecting elements are arranged at appropriate positions by combining a white light source and a spectroscope, the plurality of gas detecting elements are excited simultaneously, or such that by forming the light receiving element by a combination of a spectroscope and a multi-channel photodiode, signals from the plurality of gas detecting elements are read simultaneously.

In the present invention, as these two gas detecting means are operated simultaneously, and signals obtained respectively are inputted to the signal processing means, the property, kind and concentration of the gas are outputted. At that time, the signal processing means may be constituted by a storage device and an arithmetic unit for determining an amount of change of the signal intensity, i.e., an amount of change of the oscillation frequency detected and/or an amount of change of the intensity of fluorescence or phosphorescence detected, as well as an output display unit and the like. In addition, in a case where two kinds of signals are fetched from a plurality of gas detecting elements, respectively, signal processors may be provided separately, and the signal processing means may be constituted by a signal processor for further processing signals obtained therefrom, an output display unit, and so on. Alternatively, the signal processing means may be constituted by a signal processor, a storage device, and an arithmetic unit for simultaneously fetching two kinds of signals from the respective gas detecting elements and effecting pattern analysis at a stretch, an output display unit, and so on. By means of this signal processing means, the gas concentration is determined from the amount of change in the oscillation frequency detected and/or the amount of change in the intensity of fluorescence or phosphorescence detected.

In accordance with the gas detector of the present invention, both the adsorption-measuring type gas detection and the optical gas detection are effected. In a case where the adsorption-measuring type gas detection is effected, the reversible adsorption of the gas to be detected on the gas sensitive thin film takes place through contact between the gas sensitive thin film of the gas detecting element containing an organic dye and the gas to be detected which is adsorbable on the gas sensitive thin film, so that the mass or the density of the gas sensitive thin film containing the organic dye changes. As a result, by measuring a resultant change in the oscillation frequency of the vibrating member, it is possible to quantitatively detect the amount of adsorption of the gas to be detected.

The relationship between a change $\Delta M$ of the mass of the gas sensitive thin film and a change $\Delta F$ of the oscillation frequency in the gas detecting element in a case where the quartz resonator is used as the vibrating member can be expressed by the following formula:

$$\Delta F = (-F0^2/N \cdot \rho_q)(\Delta M/A) \quad (1)$$

where
F0: basic oscillation frequency of a quartz resonator
$\rho_q$: density of quartz
N: thickness constant
A: area Meanwhile, in the case of the SAW device, the relationship can be similarly expressed by the following formula:

$$\Delta F = -aF0^2 \Delta \rho \quad (2)$$

where
a: constant determined by the SAW device
$\Delta \rho$: change in the density of the gas sensitive thin film As is apparent from the foregoing formulae, by using a vibrating member, a change in the mass of the gas sensitive thin film in the gas detecting element is outputted quantitatively as a change in the oscillation frequency.

On the basis of the above-described relations, if the relationship between the density of the gas to be detected and an amount of change in the oscillation frequency which were obtained in advance is inputted in advance in the signal processing means, and if the difference between the oscillation frequency at the time of contact with the gas to be detected and the oscillation frequency prior to the contact with the gas to be detected is calculated by the signal processing means, it is possible to simply output the concentration of the gas to be detected quantitatively without requiring complicated correction.

In addition, as factors determining the sensitivity in the gas detecting element formed by the gas sensitive thin film and the vibrating member, the reading accuracy and stability of the oscillation frequency become important. Furthermore, the higher the basic frequency of the vibrating member, the greater change in the oscillation frequency is obtained in proportion to the square thereof. Thus, through an appropriate combination of the reading accuracy and stability of the oscillation frequency, an optimum gas detecting system can be selected.

In the present invention, in a case where optical gas detection is effected, the reversible change in the intensity of fluorescence or phosphorescence on the thin film takes place through the contact of a gas to be detected which undergoes an electronic interaction, such as an oxidizing or reducing gas to be detected, with an organic dye of the gas detecting element. By measuring the same, it is possible to optically detect the gas to be detected.

If a ratio between the intensity of fluorescence or phosphorescence from the gas sensitive thin film in contact with the gas to be detected and the intensity of fluorescence or phosphorescence from the gas sensitive thin film not in contact with the gas to be detected is determined experimentally, the following relationship can be roughly obtained:

$$F0/F = 1 + a [G] \tag{3}$$

where
a: inclination
[G]: gas concentration

This relationship is similar to the relationship concerning fluorescence and phosphorescence which is generally known among solution systems. That is, it is known that, in a solution system, the following Stern-Volver equation holds between the intensity of its fluorescence or phosphorescence and the concentration of a quencher:

$$\Phi 0/\Phi = 1 + K\tau 0 [Q] \tag{4}$$

where
$\Phi 0$: quantum efficiency of fluorescence or phosphorescence in the absence of a quencher
$\Phi$: quantum efficiency of fluorescence or phosphorescence in the presence of the quencher;
K: constant of reaction speed between a dye and the quencher
$\tau 0$: life of fluorescence or phosphorescence in the absence of the quencher
[Q]: concentration of the quencher If the intensity of the excitation light is fixed, the quantum efficiency ($\Phi 0$, $\Phi$) of fluorescence or phosphorescence is proportional to the intensity of the fluorescence or phosphorescence. If a comparison is made between Formulae (3) and (4), a similar phenomenon similar to that of a solution system occurs in gaseous and thin film systems as well, and it is considered that the gas functions as the quencher.

On the basis of the foregoing relations, if the relationship between the concentration of the gas to be detected and changes of fluorescence or phosphorescence which were determined in advance is stored in advance in the signal processing means, and the ratio between the intensity of fluorescence or phosphorescence from the gas sensitive thin film at the time of contact with the gas to be detected and the intensity of fluorescence or phosphorescence from the gas sensitive thin film at the time of noncontact with the gas sensitive thin film is calculated by the signal processing means, it is possible to simply output the concentration of the gas to be detected quantitatively without requiring complicated correction.

Furthermore, as the above-described two gas detecting methods, i.e., the adsorption-measuring type gas detecting method and the optical gas detecting method, are operated simultaneously, and the respective signals are inputted to the signal processing means, both the total amount of adsorption of the gas to be detected which can be adsorbed on the gas sensitive thin film through the adsorption-measuring type gas detecting method, and the concentration of the gas to be detected which undergoes an electronic interaction with the dye molecules in the gas sensitive thin film and has changed the intensity of fluorescence or phosphorescence through the optical gas detecting method, can be respectively measured quantitatively. In addition, the property, kind, and concentration of the gas can be outputted in a comprehensive manner. Since the aforementioned two kinds of signals are inputted simultaneously, even in a transient situation before the respective changes are saturated due to the introduction of the gas, the property, kind and concentration of the gas can be outputted on the basis of the ratio of the respective signals and an inclination of the change. Accordingly, it is possible to selectively detect quantitatively both the gas to be detected of a type which is adsorbed on the gas detecting element in the same way as an organic solvent gas, but does not change the intensity of fluorescence or phosphorescence, and the gas to be detected of a type which is adsorbed on the gas sensitive thin film in the same way as an oxidizing or reducing gas and changes the intensity of fluorescence or phosphorescence.

Hereafter, a specific description will be given of the present invention through embodiments thereof.

FIG. 1 is a basic schematic diagram of a gas detector in accordance with the present invention. In the drawing, reference numeral 1 denotes a gas detecting element in which a gas sensitive thin film containing an organic dye is formed on a piezoelectric vibrating element; 2, a reaction tank; 3, an oscillating means of the piezoelectric vibrating element; 4, a frequency detecting means; 5, a window provided in a gas passage; 6, a light emitting element; 7, a lens; 8, a filter for cutting off fluorescence or phosphorescence from the gas detecting element; 9, a light receiving element; and 10, a filter for cutting off excitation light. In addition, numeral 11 denotes a signal converter for transmitting a signal from the light receiving element 9 to a signal processing means 12.

In the gas detector having the above-described arrangement, a gas passageway for allowing a gas to flow therethrough is formed in the reaction tank 2, and the gas detecting element is disposed in the gas passageway. The arrangement provided is such that, in the gas passageway, the gas flows in the direction of arrows and is brought into contact with the gas sensitive thin film of the gas detecting element. The gas detecting element 1 is arranged to oscillate by means of the oscillating means 3 such as an oscillator circuit, and its oscillation frequency is read by the frequency detecting means 4 such as a frequency counter. As the gas to be detected is allowed to flow, molecules of the gas to be detected are adsorbed on the gas detecting element. A resultant change in the oscillation frequency allows the concentration of the gas to be determined quantitatively by the signal processing means 12 such as a computer.

Figure 2A:
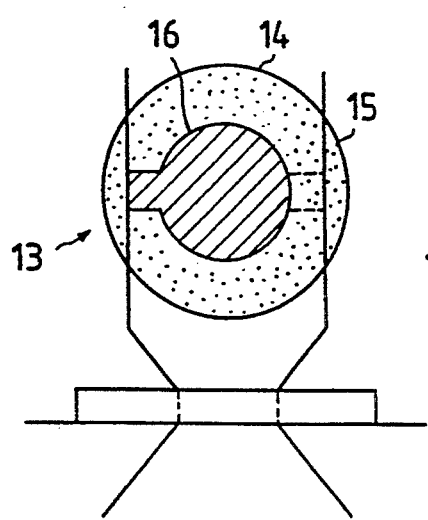
FIGS. 2a and 2b are schematic diagrams illustrating a gas detecting element using a quartz resonator in the gas detector in accordance with the present invention.
Figure 2B:
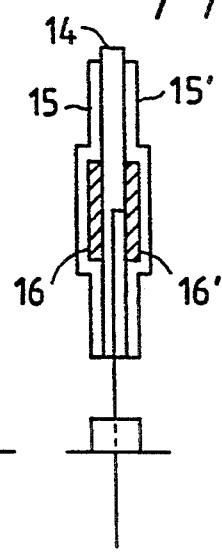

As the piezoelectric vibrating element, a 1–10 MHz quartz resonator or a 20–100 Mz SAW device is preferably used. A basic configuration of the gas detecting element 1 in a case where the quartz resonator is used is shown in FIGS. 2a and 2b. In FIGS. 2a and 2b, reference numeral 13 denotes the quartz resonator in which electrodes 16, 16' are provided on opposite sides of a quartz plate 14. Furthermore, a gas detecting thin film 15, 15' is formed thereon in such a manner as to cover the entire surfaces of the quarts plate. As the electrodes 16, 16' of the quartz resonator, those formed of silver are generally used, but aluminum, gold, titanium, or the like may be used. In particular, in a case where gold is used, corrosion resistance is excellent, so that these electrodes are suitable for measurement of an oxide gas. This quartz resonator is arranged such that the quartz plate oscillates as an a.c. voltage is applied between the electrodes 16, 16' from the oscillator circuit.

Figure 3:
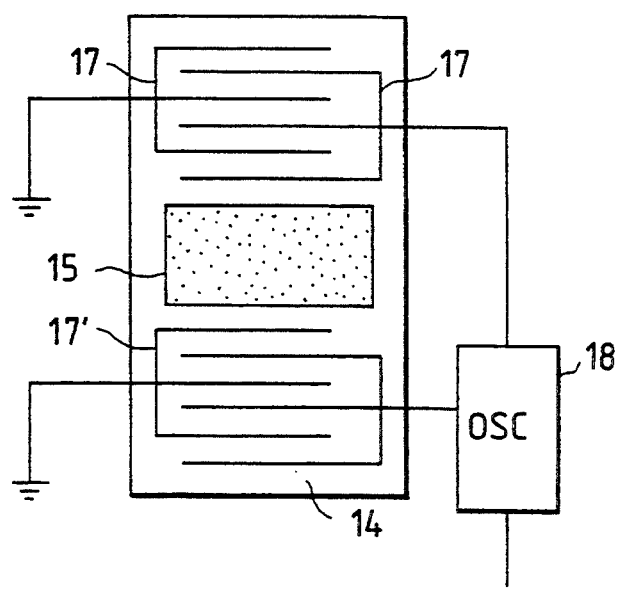
FIG. 3 is a schematic diagram illustrating a basic arrangement of a gas detecting element using a delay-line type SAW device in the gas detector in accordance with the present invention.

Next, a basic configuration of the gas detecting element 1 in a case where a SAW device is used will be described hereafter. FIG. 3 is an example of a gas detecting element using a delay-line type SAW device.

The gas detecting element using the delay-line type SAW device has the gas detecting thin film 15 provided on a surface of the quartz plate 14, and comb type electrodes 17, 17 are disposed on both sides of the thin film on the same surface. An a.c. voltage from an oscillator circuit 18 is applied to each of the comb type electrodes.

Figure 4:
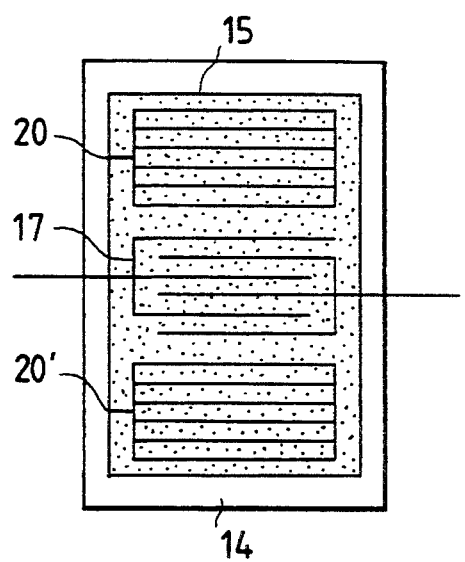
FIG. 4 is a schematic diagram illustrating a basic arrangement of a gas detecting element using a reflector type SAW device in the gas detector in accordance with the present invention.

In addition, FIG. 4 is an example of a gas detecting element using a reflector type SAW device. The gas detecting element using the reflector type SAW device is constructed such that the comb type electrode 17 is provided on the surface of the quartz plate 14, reflectors 20, 20' are disposed on both sides of the combination type electrode on the same surface, and these members are coated with the gas detecting thin film 15. In this gas detecting element as well, an a.c. voltage is applied to the comb type electrode from the oscillator circuit so as to oscillate the quartz plate.

In the present invention, as the oscillator circuit of the above-described piezoelectric vibrating element, a transistor circuit, a TTL circuit, a C-MOS circuit, or the like similar to those used for ordinary usages is used. In addition, although the surface of the piezoelectric vibrating element such as quartz is generally inactive with respect to gas, this surface is preferably subjected to surface treatment with a silane coupling agent or the like. Also, suitable for accurate detection of a gas is an oscillator circuit in which the surface of an electrode metal such as gold, aluminum, silver, titanium, or the like is similarly treated with a silane coupling agent or various types of mercaptan, sulfide, thiol, and the like and in which a measure has been devised to suppress the absorption of gas. If the oscillator circuit connected to a power supply and the quartz resonator or the SAW device are connected to each other, the overall circuit including the piezoelectric vibrating element oscillates at an oscillation frequency determined by the characteristic inherent to the respective piezoelectric vibrating element. Furthermore, if the gas to be detected is adsorbed on the gas detecting thin film 15, oscillating conditions change due to a resultant increase in the mass of the gas detecting thin film 15, so that the oscillation frequency decreases reversibly. Consequently, it is possible to quantitatively measure the amount of gas molecules adsorbed. To measure this oscillation frequency, it suffices if an electrical signal of the oscillating means 3 is transmitted to the frequency detecting means 4 via a coaxial cable. As the frequency detecting means, it is possible to use a general universal counter. In terms of its performance, it is desired that the frequency detecting means have a reading accuracy of seven digits or more, and that, if possible, the frequency detecting means be capable of reading up to the digit of 0.1 Hz with respect to an oscillation frequency on the order of 10 MHz and up to the digit of 1 Hz with respect to an oscillation frequency of 100 MHz. In addition, it is desired that the stability of the oscillation frequency be $\pm 0.5$ Hz or thereabouts with respect to the oscillation frequency on the order of 10 MHz, or $\pm 5$ Hz or thereabouts with respect to the oscillation frequency of 100 MHz. For that reason, a highly stable electronic circuit is required as the electronic circuit used for the oscillating means. Accordingly, as for those electronic components including capacitors, resistors, coils, transistors, TTLs, and an IC such as a C-MOS that are used in the oscillator circuit, it is desirable to use those having a small frequency dependence dow to the oscillation frequency of the piezoelectric vibrating element.

In addition, as for the cables connecting the piezoelectric vibrating element to the oscillating means, and the oscillating means to the frequency detecting means, it is necessary to take into account the inductance, capacitance, and resistance so as to prevent noise and the rounding of a waveform. Hence, it is desirable to use a wire braid based on as practically large cables as possible and coaxial cables adjusted to the frequency.

The space in the reaction tank 2 for allowing the gas to flow therethrough is desirably as small as possible so that the gas to be detected can be filled as speedily as possible and the response speed can be increased. In addition, a material having low adsorptivity and excellent corrosion resistance, such as Teflon, polypropylene, quartz, and stainless steel, is desirable as a material constituting the reaction tank.

Figure 5:
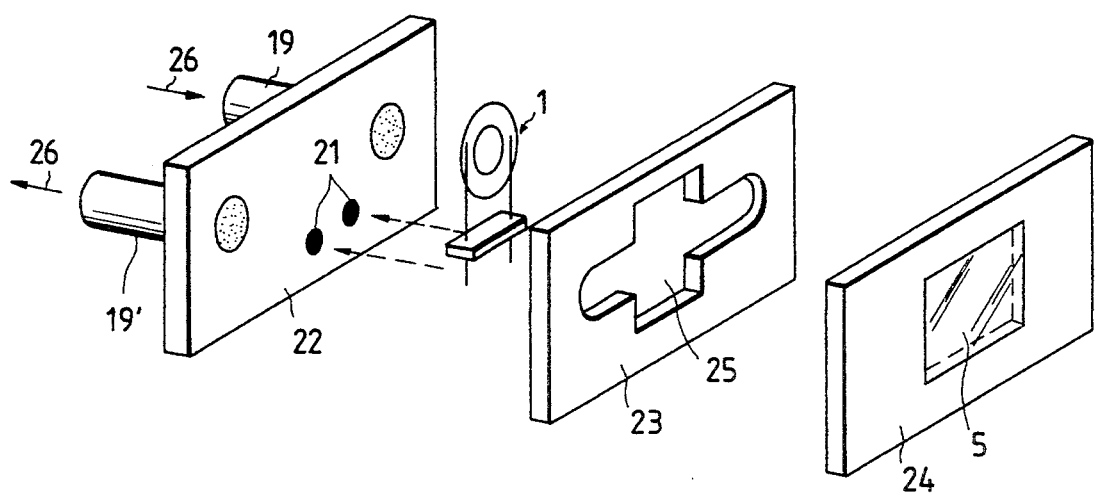
FIG. 5 is a schematic diagram illustrating a basic arrangement of a reaction tank for a gas detecting element using a quartz resonator in the gas detector in accordance with the present invention.

FIG. 5 is an exploded perspective view of a reaction tank of the reaction tank using a quartz resonator. In the drawing, reference numerals 22, 23, and 24 respectively denote a first gas reaction tank member, a second gas reaction tank member, and a third reaction tank member, which are laminated to form the reaction tank. The first reaction tank member is provided with a gas inlet port 19 and a gas outlet port 19', and electrode terminals 21 for being made electrically conductive with electrodes of the gas detecting element 1 are fixed thereon. A gas passageway 25 is formed in the second gas reaction tank member, while a window 5 is provided in the third gas reaction tank member so that a light transmissive area is formed with respect to the gas detecting element 1. The window 5 is covered with a quartz plate, for example. It should be noted that reference numeral 26 denotes the flow of the gas.

By arranging the reaction tank in a laminated form as shown in FIG. 5, it is possible to arrange a reaction tank with a small dead volume relatively easily. The piezoelectric vibrating element such as the quartz resonator responds sensitively to a change in the external pressure and temperature, so that its oscillation frequency shifts or drifts. Accordingly, in order to accurately measure the change in oscillation frequency, it is desirable to fix a flow rate of the gas to be detected, or use a reference piezoelectric vibrating element for correcting a temperature drift. With respect to the former case, if a gas pipeline in which a four-way valve is disposed at two locations, as shown in FIG. 6, is used to allow pure air and the gas to be detected to flow alternately, this arrangement is effective for the purpose of fixing the flow rate and reducing the dead volume at the time of a changeover of the gas.

Figure 6:
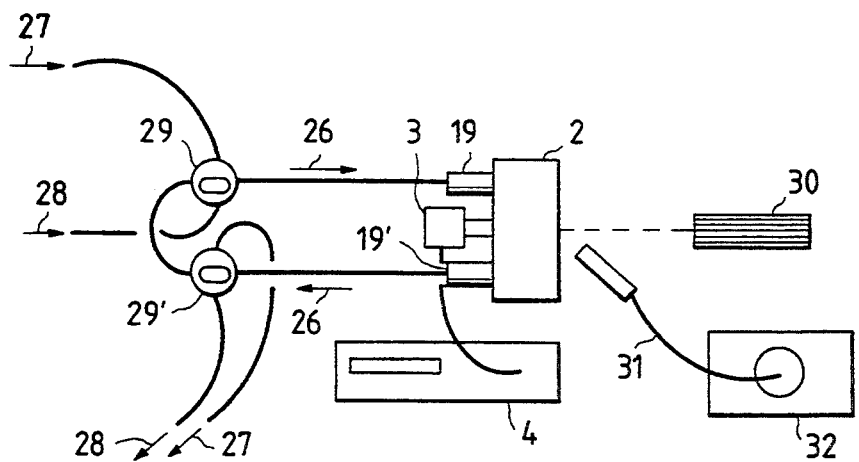
FIG. 6 is a schematic diagram illustrating a basic arrangement including a gas passageway of the gas detector in accordance with the present invention.

It should be noted that FIG. 6 is a schematic diagram illustrating a basic configuration including a gas pipeline in accordance with the present invention. In the drawing, reference numeral 2 denotes the gas reaction tank; 3, the oscillating means; and 4, the frequency detecting means. Meanwhile, reference numerals 29 and 29' denote four-way valves for changing over the passageway of the gas. Reference numeral 30 denotes an excitation light source; 31, an optical fiber; and 32, a multi-channel photodiode for receiving fluorescence or phosphorescence. In the case of this schematic diagram, a gas 28 to be detected is introduced to the four-way valve 29, and is conducted via the gas inlet port 19 of the reaction tank into the reaction tank, as shown by the arrow of the gas flow 26. The gas to be detected from the reaction tank reaches the four-way valve 29' from the gas outlet port 19', and flows in the direction of the arrow. Meanwhile, pure gas 27 enters the four-way valve 29, reaches the four-way valve 29' without passing through the reaction tank, and flows out in the direction of the arrow. If the four-way valves 29 and 29' are changed over, the flow of the aforementioned pure gas 27 and the gas 28 to be detected is changed over, and the pure gas passes through the reaction tank.

On the other hand, if the quartz resonator is used as the piezoelectric vibrating element with respect to the latter case, i.e., in a case where the reference piezoelectric vibrating element for correcting a temperature drift is used, the problem can be overcome by eliminating the difference in the oscillation frequency of the resonator forming the gas sensitive thin film if a reference resonator of the same quality is disposed in the vicinity of the reaction tank and is oscillated, or if a resonator not forming the gas sensitive thin film is disposed in the reaction tank and is oscillated. In addition, in the case where the resonator not provided with the gas sensitive thin film is used for reference, there is an advantage in that noise components which are generated can be eliminated by allowing the same to be adsorbed on the substrate and electrodes of the quartz resonator. Meanwhile, in a case where the SAW device is used as the piezoelectric vibrating element, a separate element may be provided in a similar manner, or reference electrode wiring may be provided on the same substrate so as to effect simultaneous oscillation.

Meanwhile, in FIG. 1, excitation light issuing from the light emitting element 6 is focused by the lens 7, passes through the filter 8, and is applied to the gas detecting element 1. As a result, fluorescence or phosphorescence is generated from the gas sensitive thin film of the gas detecting element 1. The fluorescence or phosphorescence thus generated reaches the light receiving element 9 via the filter 10, and is converted to an electrical signal by the signal converter 11. In this case, when the gas to be detected is brought into contact with the gas detecting element 1, the intensity of the fluorescence or phosphorescence issued from the gas detecting element 1 changes, thereby allowing the concentration of the gas to be detected as an electrical signal.

The lens 7 is used to prevent the light issued from the light emitting element 6 from diverging and to effectively focus the light on the gas detecting element 1, and this lens 7 is effective in strengthening the fluorescence or phosphorescence issued from the gas detecting element 1. The lens 7 may be arranged integrally with the light emitting element 6. There are cases where, in addition to the light having a wavelength range acting as excitation light, light having a longer wavelength is included in the light issued from the light emitting element 5. For example, in the case of a light emitting element using a GaAs material, photoluminescence having a small peak in a wavelength longer than a main emission wavelength is emitted, although in a small amount, together with the light of the main emission wavelength. The peak intensity of this light is usually not more than one millionth as compared with the peak intensity of the main emission wavelength, but this light can become noise when fluorescence or phosphorescence is measured. To eliminate such light which becomes noise, the filter 8 for cutting off light on a longer wavelength side than fluorescence or phosphorescence components is inserted. In that case, as shown in FIG. 1, the filter 8 is inserted at a slightly inclined angle so that the light reflected from the surface of the filter 8 will not return to a light emitting portion of a semiconductor laser element. In addition, in a case where a gas laser such as a He-Ne laser or an argon laser is used, the light of other modes is similarly generated, although in a small amount, in addition to the light of the basic wavelength, so that it is desirable to provide the filter 8, as necessary. Meanwhile, in a case where white light is used by subjecting the light to spectral diffraction, there are cases where diffracted light of higher order is mixed in the direction of a slit in diffraction using a spectroscope. In such a case, it is necessary that the filter 8 serves as a bandpass filter.

The filter 10 acts to prevent the excitation light issued from the light emitting element 6 from entering the light receiving element 9 after being reflected from the gas detecting element 1 or being scattered. Accordingly, even in cases where the light receiving element 9 has sensitivity to the excitation light, by preventing the excitation light or scattered light by means of the filter 10, the proportion of fluorescence or phosphorescence, of the light made incident upon the light receiving element 9, becomes large, thereby making it possible to obtain a signal having less noise.

To allow fluorescence or phosphorescence to effectively converge, a lens may be placed in front of the light receiving element 9 or the filter 10, or an assembly in which a lens and a light receiving element are formed integrally may be used. Meanwhile, in a case where a spectroscope and a photodiode array are used as a light receiving device, the lens and the spectroscope are arranged in front of the light receiving element. In addition, in a case where a diffraction grating is formed in the shape of a concave mirror, the lens may be omitted. The application of the excitation light to the piezoelectric vibrating element can affect the oscillation frequency even in the case of both the quartz resonator and the SAW device. Accordingly, the excitation light needs to be applied continuously or continually with a cycle of 1 Hz or more. In addition, if dye molecules existing on a metal electrode are excited with laser light or the like, unlike the case of dye molecules existing on an insulator, the fluorescence spectrum shifts or the wavelength width becomes broad due to the effect of the substrate. Accordingly, in a case where the gas sensitive thin film on the quartz resonator, for instance, is excited, it is desirable to avoid application of the excitation light to the electrode 16 in FIG. 2 and apply the excitation light to its surrounding portion.

Figure 7:
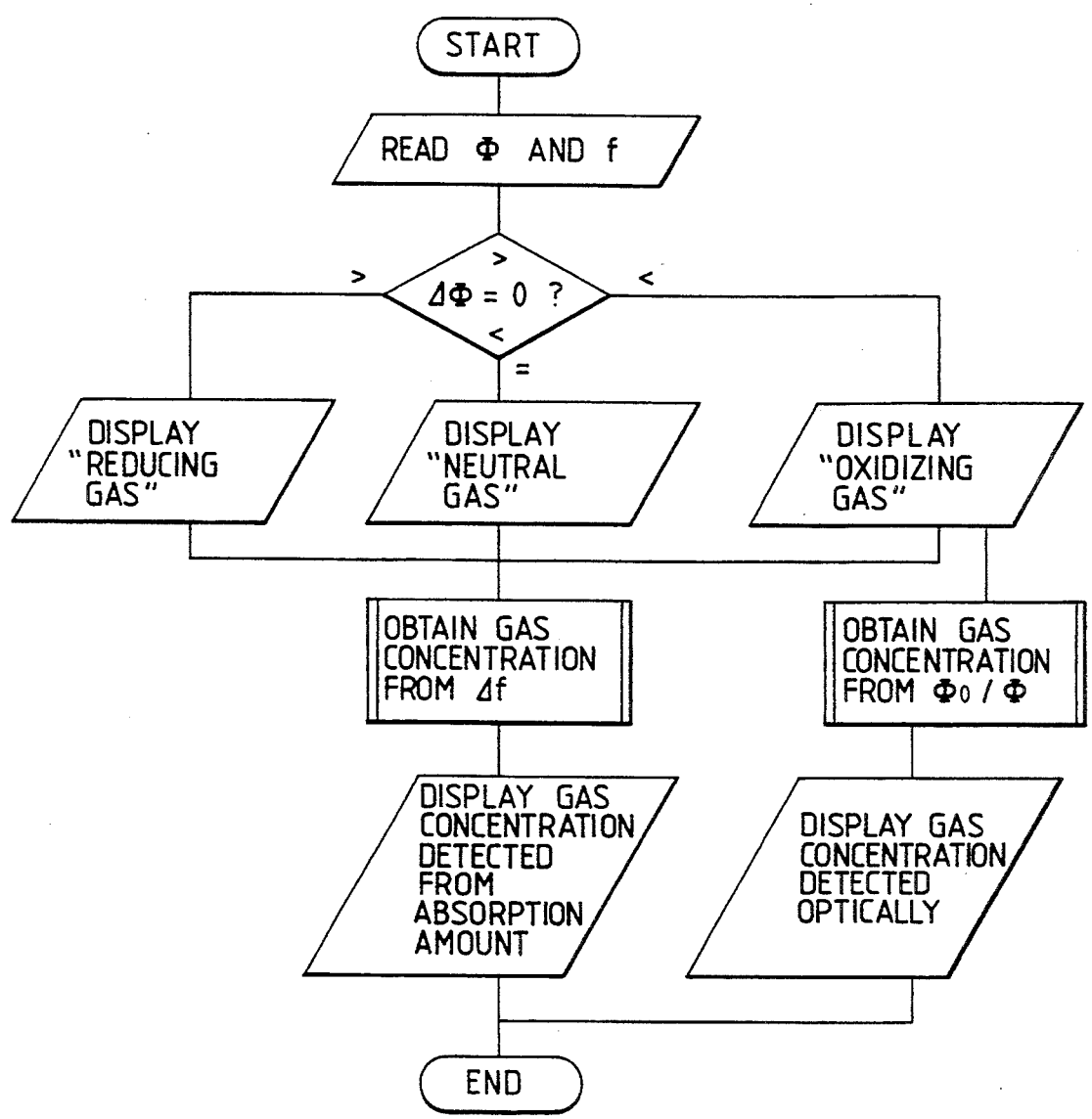
FIG. 7 is a flowchart for signal processing in a signal processing system in the case where a donor type dye is used as a gas sensitive thin film in the gas detector in accordance with the present invention.
Figure 8:
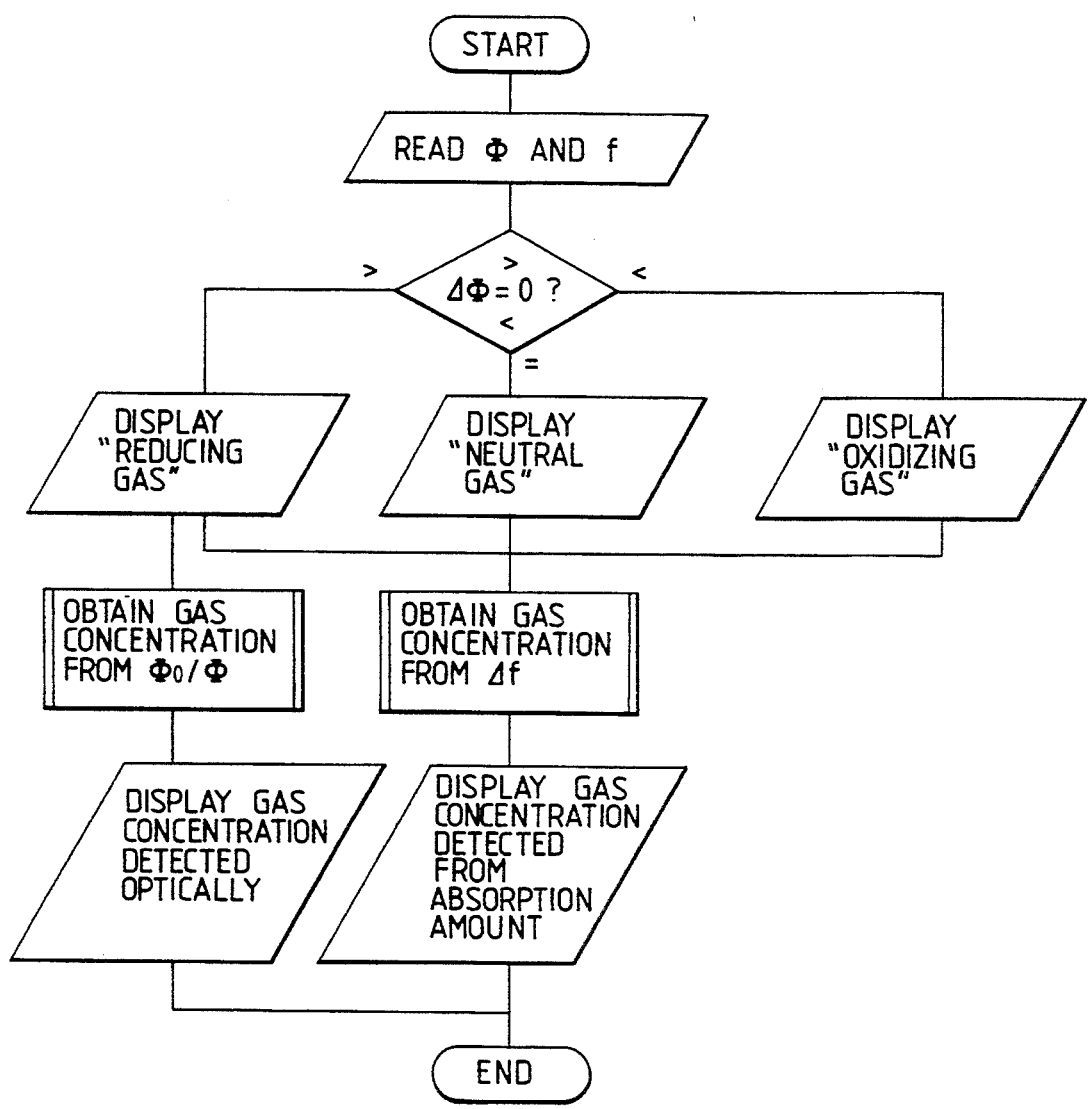
FIG. 8 is a flowchart for signal processing in the signal processing system in the case where an acceptor type dye is used as the gas sensitive thin film in the gas detector in accordance with the present invention.

The signal processing means 12 used in the present invention suffices if it is provided with a simple arithmetic function and a storage function. FIGS. 7 and 8 show flowcharts for signal processing by the signal processing means used in the present invention. FIG. 7 shows a case where a donor dye such as squarylium is used as the gas sensitive thin film, while FIG. 8 shows a case where an acceptor type dye is used as the gas sensitive thin film is used.

The signals from the two gas detecting means are outputted as the property, kind, and concentration of a gas in accordance with the flowcharts shown in these drawings. In addition, if data has been stored, it is possible to measure the concentration of a mixed gas after separating it. In the case where the donor type dye such as squarylium is used in the gas detecting element, as shown in FIG. 7, the donor type dye exhibits a property that fluorescence from the gas sensitive thin film decreases with respect to an oxidizing gas, but increases with respect to a reducing gas. Accordingly, with respect to the oxidizing gas, both the concentration of the gas obtained from an amount of absorption and the concentration of the gas obtained optically are determined, as shown in FIG. 7. Meanwhile, with respect to a change in the intensity of fluorescence or phosphorescence, a flowchart in which a converse determination is made can be applied, as shown in FIG. 8. Although it has been found that there are cases where a slightly different determination is made depending on kinds of dye, such as those which undergo extreme changes in the intensity of fluorescence or phosphorescence with respect to a particular gas, flowcharts similar to those of FIGS. 7 and 8 can be basically used.

Specifically with respect to FIG. 7, the value of an oscillation frequency sent from the frequency detecting means 4 to the signal processing means 12 is monitored for each fixed time duration (e.g. 10 seconds), and if a value thus obtained is within an arbitrary time duration (e.g. one minute) and represents a decline from a value for an earlier arbitrary time duration (i.e., a totalized value for the arbitrary time durations is subtracted from a value for an earlier arbitrary time duration, and if that value is negative), the presence of the gas to be detected is recognized. Accordingly, if a comparison is made between values of the intensity of fluorescence during two identical arbitrary time durations from the signal converting means 11 of the optical gas detector which was simultaneously monitoring, and if the gas to be detected is, for instance, an oxidizing gas and a change to a negative is detected, then it is determined that the gas to be detected is an oxidizing gas. In that case, values are totalized until the amount of change for each arbitrary time duration from the time when the change began becomes zero. This integral value is displayed, and the concentration of the gas to be detected is also displayed on the basis of the concentration of the oxidizing gas and the amount of adsorption as well as the concentration and a rate of change of the intensity of fluorescence, which are stored in the signal processing means 12. At the same time, it is notified that the gas detection has been completed.

Figure 9:
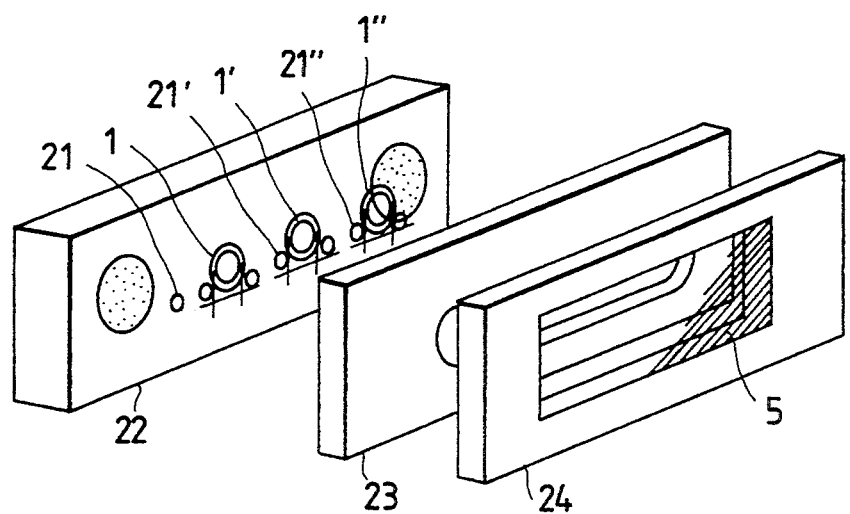
FIG. 9 is a schematic diagram illustrating a basic arrangement of the reaction tank for the gas detecting element using a plurality of quartz resonators in the gas detector in accordance with the present invention.

Meanwhile, in a case where a plurality of gas detecting elements are provided, the configuration is basically similar to the one described above. FIG. 9 is an exploded view illustrating a basic arrangement of the reaction tank of the gas detecting elements using a plurality of quartz resonators. In the drawing, reference numerals 22, 23, and 24 respectively denote the first gas reaction tank member 1, the second gas reaction tank member 2, and the third reaction tank member 3, which are laminated to form the reaction tank. The first reaction tank member is provided with a gas inlet port and a gas outlet port, and electrode terminals 21, 21', 21" for being made electrically conductive with electrodes of a plurality of gas detecting elements 1, 1', 1" are fixed thereon. A gas passageway is formed in the second gas reaction tank member, while the window 5 covered with a quartz plate is provided in the third gas reaction tank member so that a light transmissive area is formed with respect to the gas detecting elements 1, 1', 1". In the reaction tank in this illustrated case, the plurality of quartz resonators are juxtaposed in a single gas passageway and are capable of reading individual frequencies and changes of fluorescence or phosphorescence.

Figure 10:
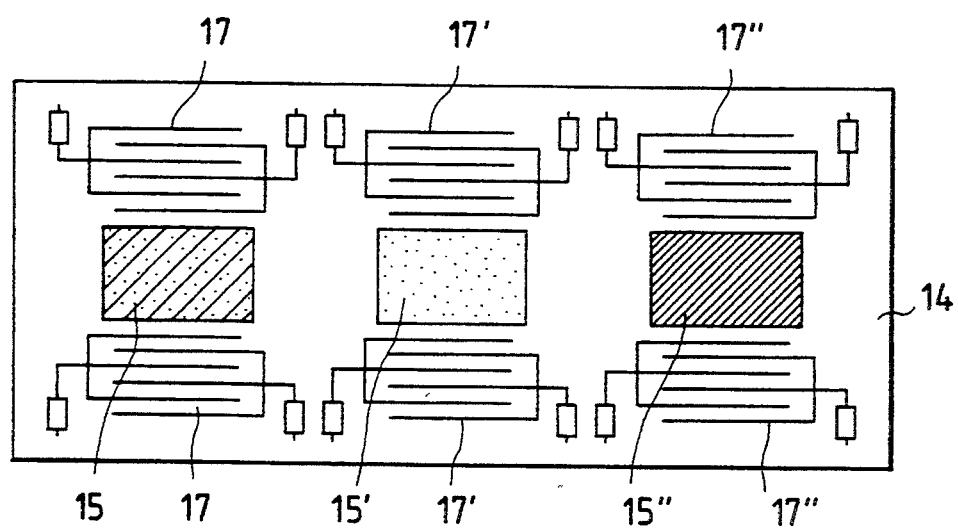
FIG. 10 is a schematic diagram illustrating a basic arrangement of a gas detecting element using the delay-line type SAW device having a plurality of gas detecting thin films in the gas detector in accordance with the present invention.

FIG. 10 is a basic schematic diagram of a gas detecting elements using a delay-line type SAW device having a plurality of gas sensitive thin films for gas detection. In this case, a plurality of gas detecting thin films 15, 15', 15" are disposed on a surface of one quartz plate 14, and comb type electrodes 17, 17', 17" are disposed on both sides of the respective gas detecting thin films on the surface. This gas detecting element is disposed in an ordinary reaction tank. In this case, provided that the excitation light source, light receiving device, oscillator circuit, and frequency reader are made different with respect to each gas detecting thin film, it suffices if those having the arrangement shown in FIG. 1 are juxtaposed for use.

Figure 11:
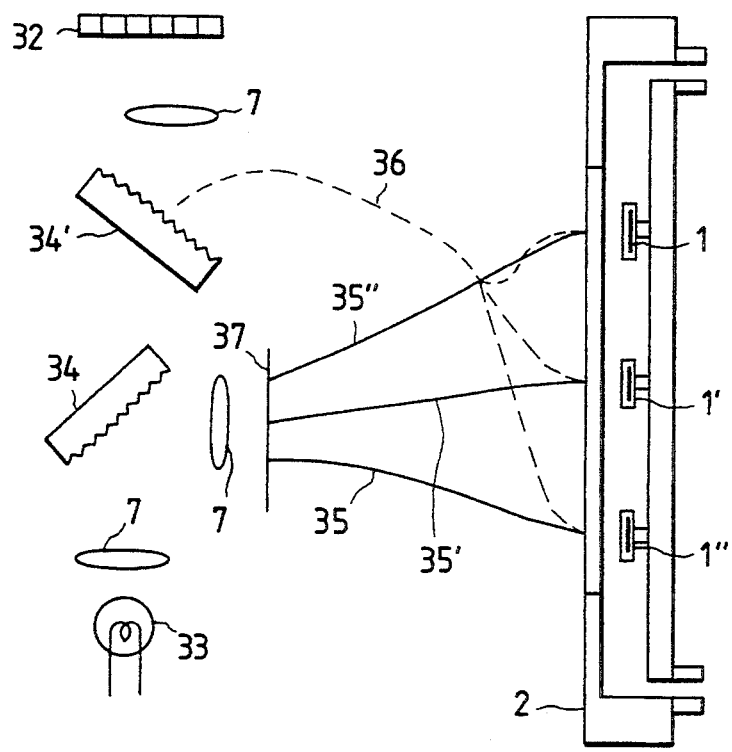
FIG. 11 is a schematic diagram illustrating a basic arrangement at a time when a white light source, a multi-channel photodiode, and a plurality of quartz resonators are used in the gas detector in accordance with the present invention.

Meanwhile, as for an optical gas detector, there are cases where a monochromatic light source such as a laser can be used jointly. Also, there are cases where an arrangement is provided such that, as shown in FIG. 11, optical fibers are used, the light source is constituted by a combination of white light and a spectroscope, which are caused to excite simultaneously, and the light receiving device is constituted by a combination of a spectroscope and a photodiode array. In this arrangement, fluorescence is fetched from the respective elements as a spectrum, or one of them is used.

It should be noted that FIG. 11 is a schematic diagram illustrating a basic configuration in a case where a white light source, a multi-channel photodiode, and a plurality of quartz resonators are used in the gas detector in accordance with the present invention. In the drawing, reference numeral denotes the reaction tank in which the plurality of gas detecting elements 1, 1', 1" are disposed. The light from a white light source 33 is made to pass through a lens 7, is spectrally diffracted by a diffraction grating 34, and is sent through respective exciting optical fibers 35, 35', 35" via another lens 7 and a slit 37 so as to be applied to the gas detecting elements. Fluorescence or phosphorescence from the gas detecting elements is made to pass through a light-receiving optical fiber 36, is spectrally diffracted by a diffraction grating 34', and is then made to pass through still another lens 7 so as to be received by the multi-channel photodiode 32.

With respect to signal processing, a most approximate result is outputted on the basis of results obtained by processing the signals from the gas detecting elements in accordance with the flowcharts shown in FIGS. 7 and 8, and on the basis of a comparison with data stored in a storage device. At that time, a result with a lowest energy obtained from statistical multivariate analysis is outputted. Such signal processing is realized by an ordinary arithmetic unit with a storage device. In addition, a method is applicable in which resultant signals from the gas detecting elements are directly projected onto a multi-dimensional coordinate system, and statistical multivariate analysis is conducted at a stretch so as to effect learning through a back propagation method or the like for a neural network model, in order to derive an optimum solution.

More specific examples will be described hereafter.

EXAMPLE 1

A squarylium dye shown by the following formula and arachic acid ($C_{19}H_{39}COOH$) were dissolved in chloroform at a molar ratio of 1:1, and a solution with a concentration of approx. $8 \times 10^{-4}$ M was prepared.

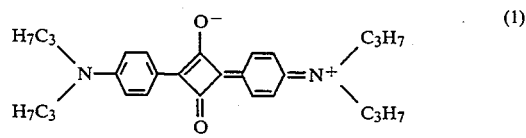

(1)

By using this solution, a 11-layered monomolecular film was accumulated on the quartz resonator using silver as 10 MHz electrodes by means of the LB film-preparing method. That is, approx. 200 m of the squarylium dye was developed on a water surface, and a gas/liquid interface for the quartz plate of the quartz resonator was raised and lowered to form a gas sensitive thin film on the quartz plate, thereby obtaining a gas detecting element.

The oscillation frequency of the quartz resonator decreased by approx. 2420 Hz as compared to the state prior to the accumulation of the gas sensitive LB film. This value represents the mass of the gas sensitive thin film.

The gas detecting element thus formed was fixed in a reaction tank provided with an adsorption-measuring type gas detector and an optical gas detector, as shown in FIG. 1. This gas detecting element was connected to an oscillating means disposed outside the reaction tank. As the oscillating means, a general oscillator circuit of a positive feedback type using a TTL was employed. As for the oscillation frequency, an oscillation signal was fetched from the oscillating means and was measured by the frequency detecting means. The frequency detecting means was a frequency counter which was capable of reading up to the digit of 0.1 Hz, and it was possible to read the oscillation frequency of the quartz resonator with a stability of ±0.1 Hz with 2 /min of pure air gas flowing through the reaction tank.

As for the configuration of the optical gas detector, a commercially available semiconductor laser element having a peak wavelength in the vicinity of 670 nm was used as the oscillating element to serve as an excitation light source. A plastic lens for converging this light was placed in front of the semiconductor laser element. Furthermore, an infrared cutoff filter for cutting off the light having a longer wavelength than 800 nm or thereabouts was disposed in an inclined state in front of the lens so that the excitation light would have an angle of incidence of about 20° with respect to the infrared cutoff filter. In addition, a commercially available silicon photodiode was used as the light receiving element, and an excitation-light cutoff filter for cutting off the excitation light having a wavelength shorter than 720 nm or thereabouts was mounted in front of it. That is, the excitation-light cutoff filter and the silicon photodiode were arranged substantially vertically with respect to the gas detecting element and 5-10 mm spaced apart from the thin film surface of the gas detecting element. When the semiconductor laser device was lit, the excitation light was applied to the gas detecting element, and fluorescence or phosphorescence emitted therefrom was received by the photodiode, and a current on the order of $10^{-9}$A flowing across the photodiode could be fetched as a 1 V voltage signal by an electric circuit of the signal converter.

In a state in which 2 /min of pure air gas (meaning air not containing the gas to be detected) was allowed to flow through the reaction tank, a changeover was effected to an air gas containing 0-10,000 ppb of $NO_2$ gas at the same flow rate, whereupon a noticeable decrease in the oscillation frequency was noted. When the air gas was changed over back to the pure air gas, the oscillation frequency of the quartz resonator recovered its original level with the exception of the component of a change in the oscillation frequency due to the irreversible adsorption of $NO_2$ gas on silver. The decrease in the oscillation frequency due to the adsorption of $NO_2$ gas on the LB film was approx. 35 Hz in the case of 800 ppm $NO_2$ gas, and approx. 6.5 Hz in the case of 150 ppb $NO_2$ gas. The amount of decrease in the frequency thus changed in proportion to the concentration of the $NO_2$ gas. It was confirmed that the $NO_2$ gas concentration can be determined quantitatively from this relation by means of the adsorption-measuring type gas detector. In addition, simultaneously with the decrease of the oscillation frequency of the quartz resonator, in the optical gas detector, the concentration of the $NO_2$ gas was confirmed quantitatively by the two detectors as a decrease of the electrical signal from the photodiode in conjunction with the decrease of fluorescence.

Furthermore, in the signal processor, as signals from the respective adsorption-measuring type and optical gas detectors were inputted thereto, a determination was made that the gas to be detected is an oxidizing gas, and results based on the two methods concerning the concentration of $NO_2$ as a candidate of the gas were displayed. The two results coincided with each other within a range of 10%.

EXAMPLE 2

In the same way as in Example 1, the adsorption-measuring type gas detector and the optical gas detector were operated simultaneously, and after the pure air gas was allowed to flow at a flow rate of 2 /min, an air gas containing 0.1-100 ppm of chloroform was allowed to flow. As a result, no change was noted in the output from the optical gas detector, so that the signal processor determined that the gas was the gas to be detected. From the adsorption-measuring type gas detector, a decrease of the oscillation frequency on the order of $10^{-1}$–$10^1$ Hz due to the adsorption of chloroform molecules on the gas sensitive thin film was inputted to the signal processor as a signal. From the relationship between the concentration of the chloroform gas and the amount of adsorption which were stored in advance, it was possible to quantitatively measure the concentration of the chloroform gas.

EXAMPLE 3

In the same way as in Example 1, the adsorption-measuring type gas detector and the optical gas detector were operated simultaneously, and after the pure air gas was allowed to flow at a flow rate of 2 /min, an air gas containing 0.01-10 ppm of $NO_2$ gas and 0.1-100 ppm of trichloroethylene was allowed to flow. As a result, a decrease of fluorescence intensity was outputted from the optical gas detector, so that the signal processor determined that an oxidizing gas exists in the gas to be detected. From the adsorption-measuring type gas detector, a decrease of the oscillation frequency on the order of $10^{-1}$–$10^2$ Hz due to the adsorption of $NO_2$ and trichloroethylene molecules on the gas sensitive thin film was inputted to the signal processor as a signal. Here, when an input was made to the effect that the gas to be detected was a mixed gas of $NO_2$ gas and trichloroethylene, it was possible to quantitatively measure the concentrations of $NO_2$ and trichloroethylene separately on the basis of the relationship between the concentrations of the respective gases and the amounts of adsorption which were stored in advance.

EXAMPLE 4

In the same way as in Example 1, the adsorption-measuring type gas detector and the optical gas detector were operated simultaneously, and after the pure air gas was allowed to flow at a flow rate of 2 /min, an air gas containing 10–10,000 ppm of ammonia was allowed to flow. As a result, there was a slight increase (up to 10%) in the output in the optical gas detector, so that the signal processor determined that the gas to be detected was a reducing gas. From the adsorption-measuring type gas detector, a decrease of the oscillation frequency on the order of $10^{-1}$–$10^2$ Hz due to the adsorption of ammonia molecules on the gas sensitive thin film was inputted to the signal processor as a signal. From the relationship between the concentration of the ammonia gas and the amount of adsorption which were stored in advance, it was possible to quantitatively measure the concentration of ammonia.

EXAMPLE 5

In the same way as in Example 1, the squarylium dye shown by the above formula and arachic acid ($C_{19}H_{39}COOH$) were dissolved in chloroform at a molar ratio of 1:1, and a solution with a concentration of approx. $8 \times 10^{-4}$ M was prepared.

By using this solution, a six-layered monomolecular film was accumulated on a 61 MHz reflector type SAW device by means of a horizontal adhesion method. That is, approx. 200 m of the aforementioned squarylium dye was developed on a water surface. Then, as the SAW device was caused to adhere to a gas/liquid interface, a gas sensitive thin film constituted by a J-aggregate of the squaryliumdye was formed on the quartz plate, thereby obtaining a gas detecting element.

The oscillation frequency of the SAW device decreased by approx. 19.5 kHz Hz as compared to the state prior to the accumulation of the gas sensitive LB film. This value represents the density per unit length of the gas sensitive thin film.

By using the gas detecting element thus formed, the adsorption-measuring type gas detector and the optical gas detector were operated simultaneously in the same way as in Example 1. This gas detecting element was connected to the oscillating means disposed outside the reaction tank. As the oscillating means, a oscillator circuit comprising transistors, resistors, capacitors, and a coil was employed. An oscillation signal was fetched from the oscillating means and an oscillation frequency was measured by the frequency detecting means. The frequency detecting means was a frequency counter which was capable of reading up to the digit of 0.1 Hz, and it was possible to read the oscillation frequency of the quartz resonator with a stability of ±0.5 Hz with 2 /min of pure air gas flowing through the reaction tank.

In this state, a changeover was effected to an air gas containing 0–10,000 ppb of $NO_2$ gas at the same flow rate, whereupon a noticeable decrease in the oscillation frequency was noted. When the air gas was changed over back to the pure air gas, the oscillation frequency of the quartz resonator recovered its original value. Decreases of approx. 275 Hz and approx. 50 Hz were respectively noted for 800 ppm $NO_2$ gas and 150 ppb $NO_2$ gas. It was thus confirmed that the amount of decrease in the frequency changes in proportion to the concentration of the $NO_2$ gas. It was hence verified that the $NO_2$ gas concentration can be determined quantitatively from this relation by means of the gas detector.

Furthermore, with respect to the decrease of fluorescence, results which were similar to those of Example 1 were obtained, and as signals from the respective means were inputted to the signal processing means, the display values of the respective $NO_2$ gas concentrations were within an error range of 10%.

EXAMPLE 6

In the same way as in Example 1, using a mixed film of the squarylium dye and arachic acid ($C_{19}H_{39}COOH$) at a molar ratio of 1:1, a 11-layered monomolecular film was accumulated on the quartz resonator using gold as 10 MHz electrodes by means of the LB film-preparing method. Consequently, a gas detecting element having a gas sensitive thin film constituted by J-aggregate(s) of the squaryliumdye was obtained.

The oscillation frequency of the quartz resonator decreased by approx. 2420 Hz as compared to the state prior to the accumulation of the gas sensitive LB film in the same way as in the case using silver as the electrodes.

The gas detecting element thus formed was fixed in the reaction tank. Then, in a state in which 2 /min of pure air gas was allowed to flow, a changeover was effected to an air gas containing 0–10,000 ppb of $NO_2$ gas at the same flow rate, whereupon a noticeable decrease in the oscillation frequency was noted. As the air gas was changed over back to the pure air gas, the oscillation frequency of the quartz resonator recovered. Changes in the oscillation frequency due to the irreversible adsorption of the gas on the electrodes were approx. one fifth as compared with those in the case of silver. As for changes in the oscillation frequency due to the gas adsorption on the LB film, decreases of approx. 35 Hz and approx. 6.5 Hz were respectively noted for 800 ppm $NO_2$ gas and 150 ppb $NO_2$ gas in a manner similar to Example 1. Although these values were identical to those of Example 1, it was possible to substantially improve the measurement accuracy. From this fact, it was confirmed again that the $NO_2$ gas concentration can be determined quantitatively by means of the adsorption-measuring type gas detector. In addition, simultaneously with the decrease of the oscillation frequency of the quartz resonator, in the optical gas detector, the concentration of the $NO_2$ gas was confirmed quantitatively by the two means as a decrease of the electrical signal from the photodiode in conjunction with the decrease of fluorescence.

Furthermore, in the signal processor, as signals from the respective adsorption-measuring type and optical gas detectors were inputted thereto, a determination was made that the gas to be detected is an oxidizing gas, and results based on the two methods concerning the concentration of $NO_2$ as a candidate of the gas were displayed. The two results coincided with each other within a range of 5%.

EXAMPLE 7

In the same way as in Example 1, using a mixed film of the squarylium dye and arachic acid ($C_{19}H_{39}COOH$) at a molar ratio of 1:1, a 3-layered monomolecular film was accumulated on the quartz resonator using gold as 10 MHz electrodes by means of the LB film-preparing method. Consequently, a gas detecting element having a gas sensitive thin film constituted by J-aggregate(s) of the squarylium dye was obtained.

The oscillation frequency of the quartz resonator decreased by approx. 660 Hz as compared to the state prior to the accumulation of the gas sensitive LB film in the same way as in the case using silver as the electrodes.

The gas detecting element thus formed was fixed in the reaction tank. Then, in a state in which 2 /min of pure air gas was allowed to flow, a changeover was effected to an air gas containing 0–10,000 ppb of NO2 gas at the same flow rate, whereupon a noticeable decrease in the oscillation frequency was noted. As the air gas was changed over back to the pure air gas, the oscillation frequency of the quartz resonator recovered. In the case where silver was used as the electrodes, if the number of layers of the LB film is small, it was impossible to accurately ascertain the change in the oscillation frequency due to the gas adsorption on the LB film since the change in the oscillation frequency due to the irreversible gas adsorption on the electrodes is large. As gold was used for the electrodes, however, it was determined that changes in the oscillation frequency due to the gas adsorption on the LB film represented decreases of approx. 3 Hz and approx. 0.75 Hz respectively for 100 ppm $NO_2$ gas and 25 ppb $NO_2$ gas. From this fact, it was confirmed again that the $NO_2$ gas concentration can be determined quantitatively by means of the adsorption-measuring type gas detector. In addition, simultaneously with the decrease of the oscillation frequency of the quartz resonator, in the optical gas detector, the concentration of the $NO_2$ gas was confirmed quantitatively by the two means as a decrease of the electrical signal from the photodiode in conjunction with the decrease of fluorescence. In addition, as the number of layers of the LB film was reduced, it was possible to increase the response speed of the signals of the two means by about three times.

In the signal processor, as signals from the respective adsorption-measuring type and optical gas detectors were inputted thereto, a determination was made that the gas to be detected is an oxidizing gas, and results based on the two methods concerning the concentration of $NO_2$ as a candidate of the gas were displayed. The two results coincided with each other within a range of 5%.

EXAMPLE 8

Prior to the accumulation of the LB film, a 10 MHz quartz resonator using gold as its electrodes was treated for 15 minutes in a mixed solution of bicyclohexyl, carbon tetrachloride, and chloroform containing $1\times10^{-4}$M octadecyl trichloroethylene, and was further treated for 20 minutes in a mixed solution of bicyclohexyl and chloroform containing $2\times10^{-2}$M octadecyl mercaptan, thereby accumulating a two-layered monomolecular film in a manner similar to that of Example 7. As a result, a gas detecting element having a gas sensitive thin film constituted by the J-aggregate(s) of the squarylium dye was obtained.

The gas detecting element thus formed was fixed in the reaction tank. Then, in a state in which 2 /min of pure air gas was allowed to flow, a changeover was effected to an air gas containing 0–10,000 ppb of $NO_2$ gas at the same flow rate, whereupon a noticeable decrease in the oscillation frequency was noted. As the air gas was changed over back to the pure air gas, the oscillation frequency of the quartz resonator recovered. As compared with Example 7 using the quartz resonator not provided with surface treatment, components of changes in the oscillation frequency due to the irreversible adsorption of the gas on the substrate were reduced to one half, making it possible to read with higher accuracy the changes of the oscillation frequency due to the gas adsorption on the LB film. As for changes in the oscillation frequency due to the gas adsorption on the LB film, decreases of approx. 2 Hz and approx. 0.5 Hz were respectively noted for 100 ppm $NO_2$ gas and 25 ppb $NO_2$ gas. From this fact, it was confirmed again that the $NO_2$ gas concentration can be determined quantitatively by means of the adsorption-measuring type gas detector. In addition, simultaneously with the decrease of the oscillation frequency of the quartz resonator, in the optical gas detector, the concentration of the $NO_2$ gas was confirmed quantitatively by the two means as a decrease of the electrical signal from the photodiode in conjunction with the decrease of fluorescence.

In the signal processor, as signals from the respective adsorption-measuring type and optical gas detectors were inputted thereto, a determination was made that the gas to be detected is an oxidizing gas, and results based on the two methods concerning the concentration of $NO_2$ as a candidate of the gas were displayed. The two results coincided with each other within a range of 4%.

EXAMPLE 9

Prior to the accumulation of the LB film, the 10 MHz quartz resonator using gold as its electrodes was treated for 15 minutes in the vapor of hexamethyldisilazane, and was further treated for 20 minutes in a chloroform solution containing $2\times10^{-2}$M octyl sulfide, thereby accumulating a two-layered monomolecular film in the same way as in Example 7. As a result, a gas detecting element having a gas sensitive thin film constituted by the J-aggregate(s) of the squarylium dye was obtained.

The gas detecting element thus formed was fixed in the reaction tank. Then, in a state in which 2 /min of pure air gas was allowed to flow, a changeover was effected to the air gas containing 0–10,000 ppb of $NO_2$ gas at the same flow rate, whereupon it was possible to suppress the components of changes in the oscillation frequency due to the irreversible adsorption of the gas on the substrate in the same way as in Example 8. Thus, it was possible to read with high accuracy the changes in the oscillation frequency due to the gas adsorption on the LB film.

In the signal processor, as signals from the respective adsorption-measuring type and optical gas detectors were inputted thereto, a determination was made that the gas to be detected is an oxidizing gas, and results based on the two methods concerning the concentration of $NO_2$ as a candidate of the gas were displayed. The two results coincided with each other within a range of 4% in the same way as in Example 8.

EXAMPLE 10

Figure 12:
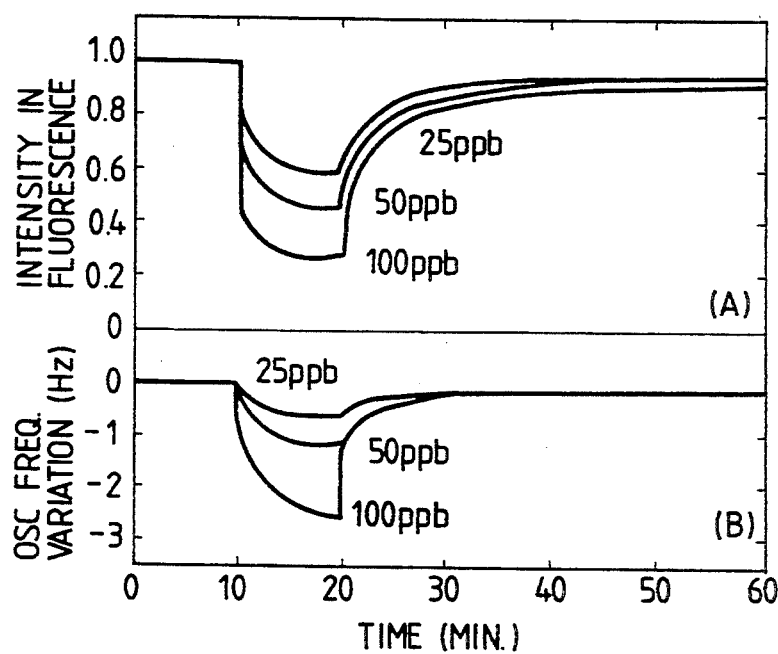
FIG. 12 is a graph on changes of a fluorescence intensity and oscillation frequency outputted from an $NO_2$ gas when a squarylium dye was used as the gas sensitive thin film in a gas detector in accordance with Example 10.

A He-Ne laser was used as an excitation light source, and the optical fibers, the diffraction grating, and the photodiode array (multi-channel photodiode) which are shown in FIG. 11 were used as the light receiving element, which was arranged to output a fluorescence intensity of 770 nm. The gas detecting element used was provided with a gas sensitive film in which a mixed film of the squarylium dye and arachic acid at a molar ratio of 1:1 was accumulated in three layers on the quartz resonator using gold in the same way as in Example 7. The adsorption-measuring type gas detector and the optical gas detector were operated simultaneously, and after the pure air gas was allowed to flow at a flow rate of 2 /min, an air gas containing 0.1–1000 ppm of chloroform was allowed to flow. As a result, in the optical gas detector, a noticeable decline in the fluorescence intensity was observed 70 as a change in the intensity of the 770 nm signal. In addition, a noticeable decline in the oscillation frequency was noted in the adsorption-measuring type gas detector which effected measurement simultaneously. Furthermore, as the gas was changed over back to the pure air gas, the two signals recovered their original values. Incidentally, changes of signals from the two gas detectors at the time when the pure air gas containing 100, 50, and 25 ppb NO$_2$ was allowed to flow are shown in FIG. 12. When these signals were inputted to the signal processor, a determination was made that the gas to be detected was an oxidizing gas, and results based on the two methods concerning the concentration of NO$_2$ as a candidate of the gas were displayed. The two results coincided with each other within a range of 4%.

EXAMPLE 11

Figure 13:
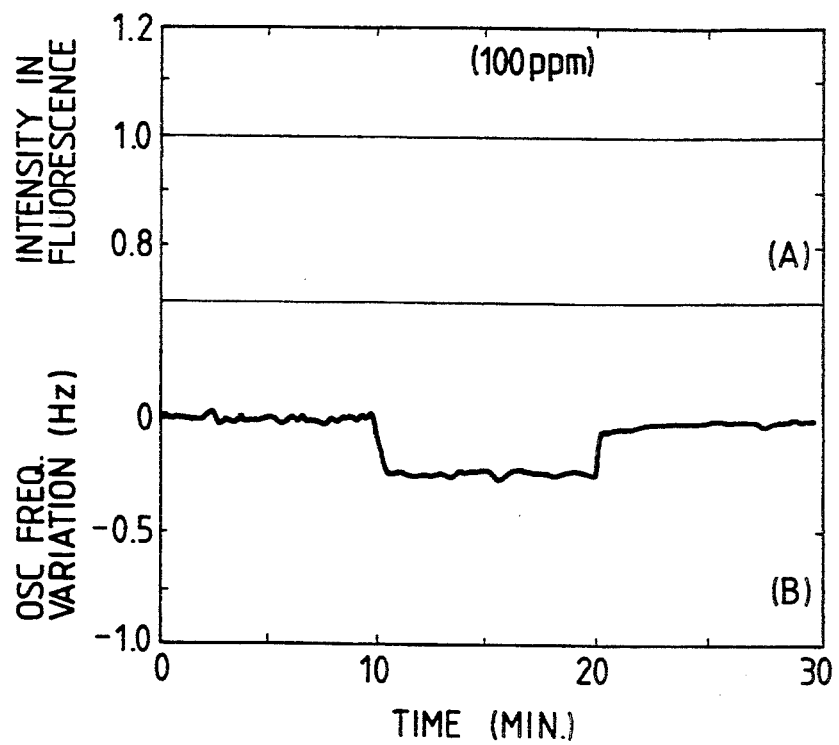
FIG. 13 is a graph on changes of a fluorescence intensity and oscillation frequency outputted from a trichloroethylene gas when the squaryliumdye was used as the gas sensitive thin film in a gas detector in accordance with Example 11.

In the same way as in Example 10, the adsorption-measuring type gas detector and the optical gas detector were operated simultaneously, and after the pure air gas was allowed to flow at a flow rate of 2 /min, an air gas containing 0.1–1000 ppm of trichloroethylene was allowed to flow. As a result, no change was noted in the output from the optical gas detector, so that the signal processor determined that the gas to be detected was a neutral gas. From the adsorption-measuring type gas detector, a decrease of the oscillation frequency on the order of $10^{-1}$–$10^1$ Hz due to the adsorption of trichloroethylene molecules on the gas sensitive thin film was inputted to the signal processor as a signal. From the relationship between the concentration of the trichloroethylene gas and the amount of adsorption which were stored in advance, it was possible to quantitatively measure the concentration of the trichloroethylene gas. Incidentally, changes of signals from the two gas detectors at the time when the pure air gas containing 100 ppb trichloroethylene was allowed to flow are shown in FIG. 13.

EXAMPLE 12

Figure 14:
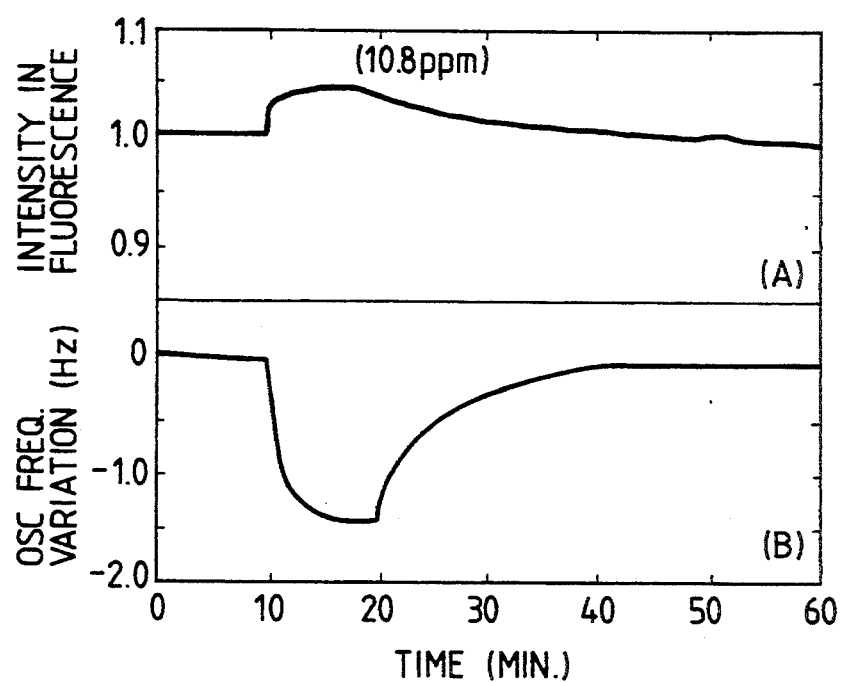
FIG. 14 is a graph on changes of a fluorescence intensity and oscillation frequency outputted from an ammonia gas when the squarylium dye was used as the gas sensitive thin film in a gas detector in accordance with Example 12.

In the same way as in Example 10, the adsorption-measuring type gas detector and the optical gas detector were operated simultaneously, and after the pure air gas was allowed to flow at a flow rate of 2 /min, an air gas containing 0.1–10,000 ppm of ammonia was allowed to flow. As a result, there was a slight increase (up to 5%) in the output in the optical gas detector, so that the signal processor determined that the gas to be detected was a reducing gas. From the adsorption-measuring type gas detector, a decrease of the oscillation frequency on the order of $10^{-1}$–$10^2$ Hz due to the adsorption of ammonia molecules on the gas sensitive thin film was inputted to the signal processor as a signal. From the relationship between the concentration of the ammonia gas and the amount of adsorption which were stored in advance, it was possible to quantitatively measure the concentration of ammonia. Incidentally, changes of signals from the two gas detectors at the time when the pure air gas containing 10.8 ppb ammonia was allowed to flow are shown in FIG. 14.

EXAMPLE 13

A perylene dye shown by the following formula and arachic acid (C$_{19}$H$_{39}$COOH) were dissolved in chloroform at a molar ratio of 1:5, and a solution with a concentration of approx. $4 \times 10^{-4}$ M was prepared.

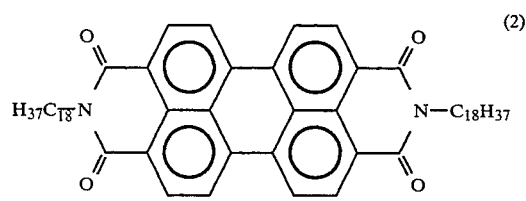

By using this solution, a three-layered monomolecular film was accumulated on the quartz resonator using silver as 10 MHz electrodes by means of the LB film-preparing method. That is, approx. 200 m of the perylene dye was developed on a water surface, and a gas/liquid interface for the quartz plate of the quartz resonator was raised and lowered to form a gas sensitive thin film on the quartz plate, thereby obtaining a gas detecting element.

The oscillation frequency of the quartz resonator decreased by approx. 390 Hz as compared to the state prior to the accumulation of the gas sensitive LB film. This value represents the mass of the gas sensitive thin film.

Figure 15:
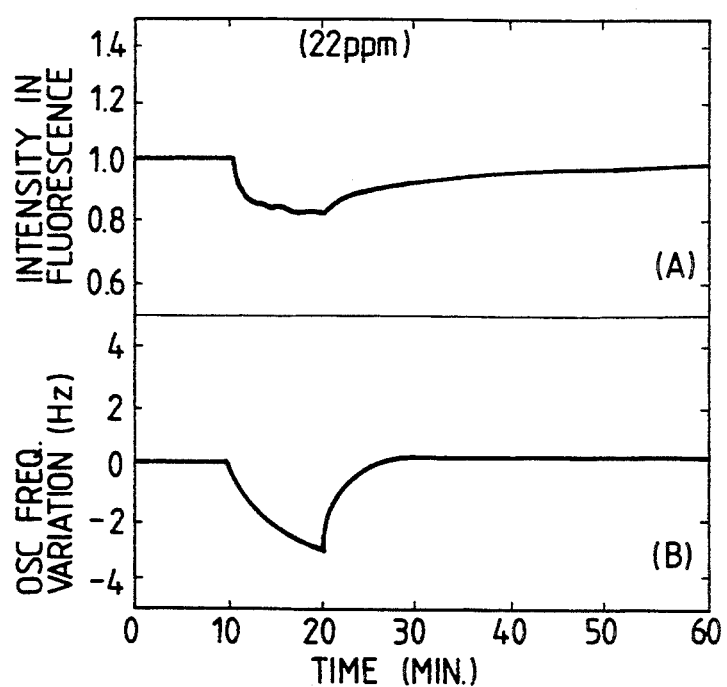
FIG. 15 is a graph on changes of a fluorescence intensity and oscillation frequency outputted from the ammonia gas when the perylene dye was used as the gas sensitive thin film in a gas detector in accordance with Example 13.

The gas detecting element thus formed was fixed in the reaction tank. Then, using an argon laser as an excitation light source, the adsorption-measuring type gas detector and the optical gas detector were operated simultaneously, and after 2 /min of pure air gas was allowed to flow, an air gas containing 1–10,000 ppb of ammonia gas was allowed to flow. In the optical gas detector, a peak in fluorescence from the perylene dye was noted at 690 nm, and this change in the signal intensity at 690 nm was set as an output. As a result, in the optical gas detector, a noticeable decline in the fluorescence intensity was observed, while a noticeable decline in the oscillation frequency was noted in the adsorption-measuring type gas detector which effected measurement simultaneously. Furthermore, as the gas was changed over back to the pure air gas, the two signals recovered their original values. Incidentally, changes of signals from the two gas detectors at the time when the pure air gas containing 22 ppm ammonia was allowed to flow are shown in FIG. 15. When these signals were inputted to the signal processor, a determination was made on the basis of the algorithm of the signal flow-chart shown in FIG. 8 that the gas to be detected was a reducing gas, and results based on the two methods concerning the concentration of ammonia as a candidate of the gas were displayed. The two results coincided with each other within a range of 4%.

EXAMPLE 14

Figure 16:
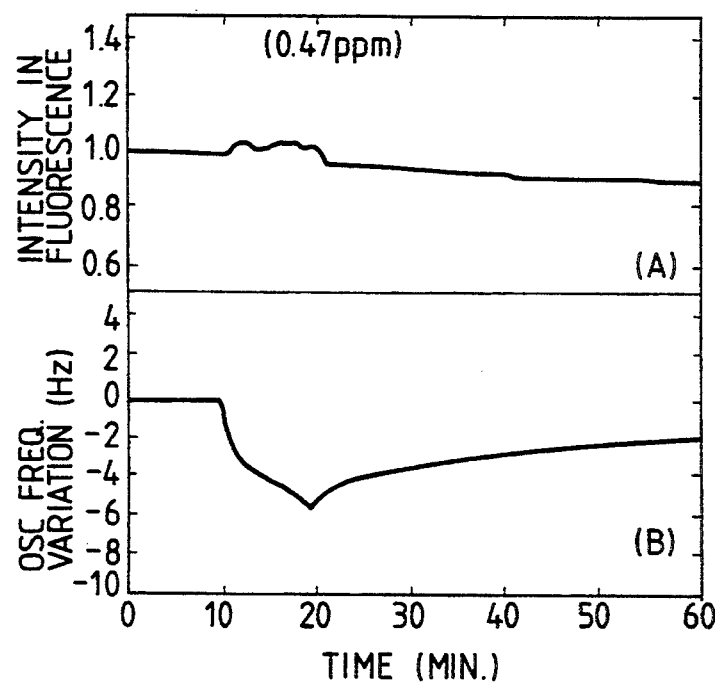
FIG. 16 is a graph on changes of a fluorescence intensity and oscillation frequency outputted from the $NO_2$ gas when the perylene dye was used as the gas sensitive thin film in a gas detector in accordance with Example 14.

In the same way as in Example 13, the adsorption-measuring type gas detector and the optical gas detector were operated simultaneously, and after the pure air gas was allowed to flow at a flow rate of 2 /min, an air gas containing 0.01–1000 ppm of NO$_2$ was allowed to flow. As a result, there was a slight increase (up to 5%) in the output in the optical gas detector, so that the signal processor determined that the gas to be detected was an oxidizing gas. From the adsorption-measuring type gas detector, a decrease of the oscillation frequency on the order of $10^{-1}$–$10^2$ Hz due to the adsorption of NO$_2$ molecules on the gas sensitive thin film was inputted to the signal processor as a signal. From the relationship between the concentration of the NO$_2$ gas and the amount of adsorption which were stored in advance, it was possible to quantitatively measure the concentration of NO$_2$. Incidentally, changes of signals from the two gas detectors at the time when the pure air gas containing 0.47 ppm NO$_2$ was allowed to flow are shown in FIG. 16.

EXAMPLE 15

A gas detecting element having a sensitive gas thin film constituted by the J-aggregate(s) of the squarylium dye formed in the same way as in Example 7, a gas detecting element having a gas sensitive thin film constituted by the perylene dye formed in the same way as in Example 13, and a 10 MHz quartz resonator not provided with a gas sensitive thin film and having gold as its electrodes were fixed in the reaction tank shown in FIG. 9. A He-Ne laser was used as the excitation light source for the gas detecting element constituted by the J-aggregate(s) of the squarylium dye, an argon laser was used for the gas detecting element constituted by the perylene dye, and excitation light was not applied to the quartz resonator not provided with the gas sensitive thin film. In addition, the optical fiber, the diffraction grating, and the photodiode array which are shown in FIG. 11 and were similar to Example 10 were used as the light receiving element. Pure air gas containing 0.01–10000 ppb of NO$_2$ was allowed to flow through the gas detecting system which comprised this optical gas detector and the adsorption-measuring type gas detector in which three sets of oscillator circuit and frequency counter similar to those of Example 1 were provided for the respective vibrators. Consequently, in the optical gas detector, a noticeably decreased output in the gas detecting element having the gas sensitive thin film constituted by the J-aggregate(s) of the squarylium dye, and a slightly increased output in the gas detecting element having the gas sensitive thin film constituted by the perylene dye were observed when 770 and 690 nm were set as the signal intensity, respectively. Meanwhile, in the adsorption-measuring type gas detector as well, an output indicating a decrease in oscillation frequency was obtained from the respective vibrators. When a signal in which a signal of the vibrator not provided with the gas sensitive thin film was subtracted from the signals of the two gas detecting elements was set as each output, and was combined with the signal of the optical gas detector and inputted to the signal processor, a determination was made that the gas to be detected was an oxidizing gas. The NO$_2$ gas was pointed out as the most probable candidate, and its concentration was outputted simultaneously.

EXAMPLE 16

An ar gas containing 0.1–10000 ppb of ammonia was allowed to flow through the gas detecting system comprising the gas detecting elements, the optical gas detector, and the adsorption-measuring type gas detector which were similar to those of Example 15. Consequently, in the optical gas detector, a slightly increased output in the gas detecting element having the gas sensitive thin film constituted by the J-aggregate(s) of the squarylium dye, and a noticeably increased output in the gas detecting element having the gas sensitive thin film constituted by the perylene dye were observed when 770 and 690 nm were set as the signal intensity, respectively. Meanwhile, in the adsorption-measuring type gas detector as well, an output indicating a decrease in oscillation frequency was obtained from the respective vibrators. When, in the same way as in Example 15, a signal in which a signal of the vibrator not provided with the gas sensitive thin film was subtracted from the signals of the two gas detecting elements was set as each output, and was combined with the signal of the optical gas detector and inputted to the signal processor, a determination was made that the gas to be detected was a reducing gas. The ammonia gas was pointed out as the most probable candidate, and its concentration was outputted simultaneously.

EXAMPLE 17

A gas sensitive thin film constituted by the J-aggregate(s) of the squarylium dye and a gas sensitive thin film constituted by the perylene dye were respectively formed on two of three gas detecting elements each having a 49 MHz delay-line type SAW device on a substrate, and these gas detecting elements were fixed in the reaction tank. The He-Ne laser was used as the excitation light source for the gas sensitive thin film constituted by the J-aggregate(s) of the squarylium dye, the argon laser was used for the gas sensitive thin film constituted by the perylene dye. In addition, the optical fiber, the diffraction grating, and the photodiode array which are shown in FIG. 11 and were similar to Example 10 were used as the light receiving element. Air gas containing 0.01–10000 ppb of NO$_2$ was allowed to flow through the gas detecting system which comprised this optical gas detector and the adsorption-measuring type gas detector in which three sets of oscillator circuit and frequency counter similar to those of Example 5 were provided for the respective vibrators. Consequently, in the optical gas detector, a noticeably decreased output in the gas detecting element having the gas sensitive thin film constituted by the J-aggregate(s) of the squarylium dye, and a slightly increased output in the gas detecting element having the gas sensitive thin film constituted by the perylene dye were observed when 770 and 690 run were set as the signal intensity, respectively. Meanwhile, in the adsorption-measuring type gas detector as well, an output indicating a decrease in oscillation frequency was obtained from the respective vibrators. When a signal in which a signal of the vibrator not provided with the gas sensitive thin film was subtracted from the signals of the two gas detecting elements was set as each output, and was combined with the signal of the optical gas detector and inputted to the signal processor, a determination was made that the gas to be detected was an oxidizing gas. The NO$_2$ gas was pointed out as the most probable candidate, and its concentration was outputted simultaneously.

As described above, in the gas detector in accordance with the present invention, since the irreversible adsorption of a gas to be detected on a gas sensitive thin film containing an organic dye is measured in terms of the change in the mass of the thin film and in the change of the fluorescence intensity, it is possible to simultaneously observe a physical adsorption process and an electronic interaction between the dye molecules in the gas sensitive thin film and the molecules of the gas to be detected. In addition, it is possible to detect the property, kind, and concentration of the gas to be detected, and it is possible to detect the gas by separating a component from a simple mixed gas. Furthermore, even with respect to a gas for which no data has been stored, it is possible to detect what type of component is contained in the gas. Accordingly, the gas detector in accordance with the present invention can be applied to a danger predicting system for a harmful gas in the environment.

In addition, by preparing a plurality of gas detecting elements for simultaneously operating two detecting means such as those described above, it is possible to detect a more complicated mixed gas and separate components more accurately.

With the gas detector in accordance with the present invention, the mass-measuring type gas detecting means is constituted by a simple piezoelectric vibrator and a simple frequency-measuring system of a power-saving type, while the optical gas detecting means is constituted by simple light-emitting and light-receiving elements. Accordingly, the gas detector excels in sensitivity, stability, and response speed, and is usable in a wide range of concentration. In addition, since the gas detector is easy to fabricate and is advantageous in terms of cost and as a measure against the environment, a extremely wide range of application is possible. Moreover, since both the change in mass and a change in the intensity of fluorescence or phosphorescence are utilized in the gas detection, the gas detector is resistant against electrical, magnetic, and chemical interferences.

What is claimed is:

1. A gas detector comprising:
    a gas detecting element having a vibrating member and a gas sensitive thin film disposed on said vibrating member, said thin film being adapted to generate either fluorescence or phosphorescence when irradiated with light;
    vibrating means for vibrating said vibrating member;
    frequency detecting means for detecting an oscillation frequency of said vibrating member, said oscillation frequency indicating a concentration of a gas;
    light means for radiating light to said gas sensitive thin film; and
    light detecting means for receiving the fluorescence or phosphorescence generated from said gas sensitive thin film to detect the intensity thereof, said intensity indicating a concentration of the gas.

2. A gas detector as recited in claim 1, further comprising signal processing means for determining an amount of change in the oscillation frequency detected and/or an amount of change in the intensity of the light detected.

3. A gas detector as recited in claim 2, wherein said signal processing means determines a concentration of a gas from the amount of change in the oscillation frequency detected and/or the amount of change in the intensity of the light detected.

4. A gas detector as recited in claim 1, wherein said gas detecting element is disposed in a reaction tank having a gas passageway.

5. A gas detector as recited in claim 4, wherein said reaction tank has a light transmissive area provided in face-to-face relation with said gas sensitive thin film.

6. A gas detector as recited in claim 1, wherein said gas detecting element is constituted by a monomolecular laminated film of an organic dye.

* * * * *